United States Patent
Mohan et al.

(10) Patent No.: US 10,022,263 B2
(45) Date of Patent: Jul. 17, 2018

(54) SLING-BASED TREATMENT OF OBSTRUCTIVE SLEEP APNEA

(75) Inventors: Arun Mohan, Lafayette, IN (US); Darin Schaeffer, Bloomington, IN (US); Patrick C. Melder, Marietta, GA (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 1232 days.

(21) Appl. No.: 13/550,065

(22) Filed: Jul. 16, 2012

(65) Prior Publication Data

US 2013/0056009 A1   Mar. 7, 2013

Related U.S. Application Data

(60) Provisional application No. 61/507,914, filed on Jul. 14, 2011, provisional application No. 61/533,189, filed on Sep. 10, 2011.

(51) Int. Cl.
*A61F 5/56* (2006.01)

(52) U.S. Cl.
CPC .................... *A61F 5/566* (2013.01)

(58) Field of Classification Search
CPC ........... A61B 5/00; A61B 5/48; A61B 5/4806; A61B 5/4818; A61F 2/00; A61F 2/02;
(Continued)

(56) References Cited

U.S. PATENT DOCUMENTS

| 4,024,859 A | 5/1977 | Slepyan et al. |
| 4,064,873 A | 12/1977 | Swenson |

(Continued)

FOREIGN PATENT DOCUMENTS

| WO | WO03002027 | 1/2003 |
| WO | 2007149469 | 12/2007 |

(Continued)

OTHER PUBLICATIONS

International Searching Authority, International Search Report and the Written Opinion, for Internation Application No. PCT/US2012/046923, Nov. 2, 2012, p. 1-18.

(Continued)

*Primary Examiner* — Kari Rodriquez
(74) *Attorney, Agent, or Firm* — Buchanan Van Tuinen LLC

(57) ABSTRACT

Slings, kits, and methods useful in the treatment of Obstructive Sleep Apnea (OSA) are described. An exemplary sling comprises a main body extending along a lengthwise axis and having first and second opposing ends, first and second opposing sides, and first and second opposing surfaces. Each end defines an end loop that defines a passageway extending through the main body. An exemplary method of treatment comprises creating two openings in the mandible of a patient; creating two longitudinal tunnels in the tongue of the patient; creating a transverse tunnel in the tongue of the patient; advancing a sling through the transverse tunnel; pulling each end of the sling through one of the longitudinal tunnels and through one of the openings in the mandible; pulling the tongue toward the front of the mouth or mandible; and securing the sling to a tissue to support the tongue in a new position.

12 Claims, 10 Drawing Sheets

(58) Field of Classification Search
CPC .... A61F 2/20; A61F 2/203; A61F 5/00; A61F 5/56; A61F 5/566
USPC ............ 128/846, 848, 897–899, 876; 623/9, 623/11.11, 13.11, 13.13, 14.11, 14.13; 600/37; 602/75–77; 606/203
See application file for complete search history.

(56) References Cited

U.S. PATENT DOCUMENTS

| | | | |
|---|---|---|---|
| 4,608,972 A | 9/1986 | Small | |
| 4,917,604 A | 4/1990 | Small | |
| 5,674,191 A | 10/1997 | Edwards et al. | |
| 5,988,171 A | 11/1999 | Sohn et al. | |
| 6,042,534 A * | 3/2000 | Gellman | A61F 2/0045 600/30 |
| 6,159,208 A | 12/2000 | Hovda et al. | |
| 6,397,841 B1 | 6/2002 | Kenyon et al. | |
| 6,408,851 B1 | 6/2002 | Karell | |
| 6,513,530 B2 | 2/2003 | Knudson et al. | |
| 6,513,531 B2 | 2/2003 | Knudson et al. | |
| 6,523,541 B2 | 2/2003 | Knudson et al. | |
| 6,895,963 B1 | 5/2005 | Martin et al. | |
| 6,910,483 B2 | 6/2005 | Daly et al. | |
| 6,911,002 B2 * | 6/2005 | Fierro | A61F 2/0045 600/30 |
| 6,955,172 B2 | 10/2005 | Nelson et al. | |
| 6,974,419 B1 | 12/2005 | Voss et al. | |
| 7,004,941 B2 | 2/2006 | Tvinnereim et al. | |
| 7,047,979 B2 | 5/2006 | Conrad et al. | |
| 7,063,089 B2 | 6/2006 | Knudson et al. | |
| 7,073,505 B2 | 7/2006 | Nelson et al. | |
| 7,090,672 B2 | 8/2006 | Underwood et al. | |
| 7,128,069 B2 | 10/2006 | Farrugia et al. | |
| 7,168,429 B2 | 1/2007 | Matthews et al. | |
| 7,188,627 B2 | 3/2007 | Nelson et al. | |
| 7,213,599 B2 | 5/2007 | Conrad et al. | |
| 7,216,647 B2 | 5/2007 | Lang et al. | |
| 7,255,109 B2 | 8/2007 | Knudson et al. | |
| 7,291,112 B2 | 11/2007 | Martin et al. | |
| 7,337,778 B2 | 3/2008 | Martin et al. | |
| 7,337,781 B2 | 3/2008 | Vassallo | |
| 7,360,542 B2 | 4/2008 | Nelson et al. | |
| 7,363,926 B2 | 4/2008 | Pflueger et al. | |
| 7,387,634 B2 | 6/2008 | Benderev | |
| 7,401,611 B2 | 7/2008 | Conrad et al. | |
| 7,491,200 B2 | 2/2009 | Underwood | |
| 7,607,439 B2 | 10/2009 | Li | |
| 7,644,714 B2 | 1/2010 | Atkinson et al. | |
| 7,658,192 B2 | 2/2010 | Harrington | |
| 7,669,603 B2 | 3/2010 | Knudson et al. | |
| 7,673,635 B2 | 3/2010 | Conrad et al. | |
| 7,680,538 B2 | 3/2010 | Durand et al. | |
| 7,703,460 B2 | 4/2010 | Conrad et al. | |
| 7,813,812 B2 | 10/2010 | Kieval et al. | |
| 7,827,038 B2 | 11/2010 | Richard et al. | |
| 7,827,988 B2 | 11/2010 | Matthews et al. | |
| 7,845,357 B2 | 12/2010 | Buscemi et al. | |
| 7,856,980 B2 | 12/2010 | Lang et al. | |
| 7,874,291 B2 | 1/2011 | Ging et al. | |
| 7,884,101 B2 | 2/2011 | Teegarden et al. | |
| 7,909,037 B2 | 3/2011 | Hegde et al. | |
| 7,909,038 B2 | 3/2011 | Hegde et al. | |
| 7,921,850 B2 | 4/2011 | Nelson et al. | |
| 7,934,506 B2 | 5/2011 | Woodson et al. | |
| 7,935,065 B2 | 5/2011 | Martin et al. | |
| 7,938,114 B2 | 5/2011 | Matthews et al. | |
| 7,949,400 B2 | 5/2011 | Kieval et al. | |
| 7,954,494 B1 | 6/2011 | Connor | |
| 7,955,267 B2 | 6/2011 | Voss et al. | |
| 7,975,700 B2 | 7/2011 | Frazier et al. | |
| 7,976,471 B2 | 7/2011 | Martin et al. | |
| 7,980,248 B2 | 7/2011 | Hegde et al. | |
| 7,992,564 B2 | 8/2011 | Doshi et al. | |
| 7,992,566 B2 | 8/2011 | Pflueger et al. | |
| 7,992,567 B2 | 8/2011 | Hirotsuka et al. | |
| 7,997,266 B2 | 8/2011 | Frazier et al. | |
| 7,997,267 B2 | 8/2011 | Ging et al. | |
| 8,074,655 B2 | 12/2011 | Sanders | |
| 8,096,303 B2 | 1/2012 | Dineen et al. | |
| 8,167,787 B2 | 5/2012 | Gillis | |
| 8,220,466 B2 | 7/2012 | Frazier et al. | |
| 8,220,467 B2 | 7/2012 | Sanders | |
| 8,327,854 B2 | 12/2012 | Gillis et al. | |
| 8,460,322 B2 | 6/2013 | van der Burg et al. | |
| 8,776,799 B2 * | 7/2014 | Gillis | A61F 2/00 128/848 |
| 2001/0050085 A1 | 12/2001 | Knudson et al. | |
| 2003/0111079 A1 | 6/2003 | Matthews et al. | |
| 2003/0140925 A1 | 7/2003 | Sapienza et al. | |
| 2003/0168064 A1 | 9/2003 | Daly et al. | |
| 2003/0176875 A1 | 9/2003 | Anderson et al. | |
| 2004/0006353 A1 * | 1/2004 | Bosley, Jr. | A61B 17/06109 606/151 |
| 2004/0028676 A1 | 2/2004 | Klein et al. | |
| 2004/0073272 A1 | 4/2004 | Knudson et al. | |
| 2004/0112387 A1 | 6/2004 | Lang et al. | |
| 2004/0144395 A1 * | 7/2004 | Evans | A61B 17/06066 128/885 |
| 2004/0153127 A1 | 8/2004 | Gordon et al. | |
| 2004/0187870 A1 | 9/2004 | Matthews et al. | |
| 2005/0005937 A1 | 1/2005 | Farrugia et al. | |
| 2005/0098184 A1 | 5/2005 | Conrad et al. | |
| 2005/0103339 A1 | 5/2005 | Daly et al. | |
| 2005/0126563 A1 | 6/2005 | van der Burg et al. | |
| 2005/0175665 A1 * | 8/2005 | Hunter et al. | 424/423 |
| 2005/0178384 A1 | 8/2005 | Martin et al. | |
| 2005/0217673 A1 | 10/2005 | Daly et al. | |
| 2005/0267547 A1 | 12/2005 | Knudson et al. | |
| 2005/0279365 A1 | 12/2005 | Armijo et al. | |
| 2006/0000475 A1 | 1/2006 | Matthews et al. | |
| 2006/0070626 A1 | 4/2006 | Frazier et al. | |
| 2006/0150986 A1 | 7/2006 | Roue et al. | |
| 2006/0207612 A1 | 9/2006 | Jackson et al. | |
| 2006/0235877 A1 | 10/2006 | Richard et al. | |
| 2007/0132117 A1 | 6/2007 | Truitt et al. | |
| 2007/0134085 A1 | 6/2007 | Daly et al. | |
| 2007/0144539 A1 | 6/2007 | van der Burg et al. | |
| 2007/0157928 A1 | 7/2007 | Pujol et al. | |
| 2007/0157934 A1 | 7/2007 | Lang et al. | |
| 2007/0207994 A1 | 9/2007 | Teegarden et al. | |
| 2007/0209664 A1 | 9/2007 | Paraschac et al. | |
| 2007/0209665 A1 | 9/2007 | Gillis et al. | |
| 2007/0244086 A1 | 10/2007 | Teegarden et al. | |
| 2007/0256693 A1 | 11/2007 | Paraschac et al. | |
| 2007/0287923 A1 | 12/2007 | Adkins et al. | |
| 2008/0023012 A1 | 1/2008 | Dineen et al. | |
| 2008/0027560 A1 | 1/2008 | Jackson et al. | |
| 2008/0041382 A1 | 2/2008 | Matthews et al. | |
| 2008/0041383 A1 | 2/2008 | Matthews et al. | |
| 2008/0045813 A1 | 2/2008 | Phuah et al. | |
| 2008/0053461 A1 | 3/2008 | Hirotsuka et al. | |
| 2008/0058584 A1 | 3/2008 | Hirotsuka et al. | |
| 2008/0066753 A1 | 3/2008 | Martin et al. | |
| 2008/0066765 A1 | 3/2008 | Paraschac et al. | |
| 2008/0066769 A1 | 3/2008 | Dineen et al. | |
| 2008/0091058 A1 * | 4/2008 | Bosley | A61B 17/06109 600/37 |
| 2008/0097380 A1 | 4/2008 | Li | |
| 2008/0099019 A1 | 5/2008 | Martin et al. | |
| 2008/0194953 A1 | 8/2008 | Kerber | |
| 2008/0208265 A1 | 8/2008 | Frazier et al. | |
| 2008/0251071 A1 | 10/2008 | Armitstead et al. | |
| 2009/0044814 A1 | 2/2009 | Iancea et al. | |
| 2009/0053306 A1 | 2/2009 | Agarwal et al. | |
| 2009/0060905 A1 | 3/2009 | Martin et al. | |
| 2009/0099471 A1 | 4/2009 | Broadley et al. | |
| 2009/0131923 A1 | 5/2009 | Connors et al. | |
| 2010/0004264 A1 | 1/2010 | Xiong et al. | |
| 2010/0010061 A1 | 1/2010 | Cooper et al. | |
| 2010/0016694 A1 | 1/2010 | Martin et al. | |
| 2010/0028026 A1 | 2/2010 | Inami et al. | |
| 2010/0106246 A1 | 4/2010 | Rousseau et al. | |
| 2010/0108066 A1 | 5/2010 | Martin et al. | |
| 2010/0108077 A1 | 5/2010 | Lindh et al. | |

(56) References Cited

U.S. PATENT DOCUMENTS

| | | | |
|---|---|---|---|
| 2010/0132719 A1 | 6/2010 | Jacobs et al. | |
| 2010/0144701 A1 | 6/2010 | Cooper et al. | |
| 2010/0234946 A1 | 9/2010 | Rousseau | |
| 2010/0300458 A1 | 12/2010 | Stubbs et al. | |
| 2011/0056498 A1 | 3/2011 | Lang et al. | |
| 2011/0094520 A1 | 4/2011 | Mikhailenok et al. | |
| 2011/0100376 A1 | 5/2011 | Rousseau | |
| 2011/0100378 A1 | 5/2011 | Rousseau | |
| 2011/0130249 A1 | 6/2011 | Mikhailenok et al. | |
| 2011/0144421 A1* | 6/2011 | Gillis | A61F 5/56 600/37 |
| 2011/0166673 A1* | 7/2011 | Patel | A61L 27/3633 623/23.72 |
| 2011/0183928 A1 | 7/2011 | Thede et al. | |
| 2011/0226264 A1 | 9/2011 | Friedman | |
| 2011/0245850 A1 | 10/2011 | van der Burg et al. | |
| 2011/0308530 A1 | 12/2011 | Gillis et al. | |
| 2013/0056009 A1 | 3/2013 | Mohan et al. | |
| 2013/0085546 A1 | 4/2013 | Bolea et al. | |
| 2013/0180528 A1 | 7/2013 | Zhou et al. | |
| 2013/0213409 A1 | 8/2013 | Podmore et al. | |

FOREIGN PATENT DOCUMENTS

| | | |
|---|---|---|
| WO | 2009140197 | 11/2009 |
| WO | WO2010045546 | 4/2010 |
| WO | WO2010051195 | 5/2010 |
| WO | WO2011068952 | 6/2011 |
| WO | 2011123714 | 10/2011 |

OTHER PUBLICATIONS

Woodson et al. Multicenter study of a novel adjustable tongue-advacement device for obstructive sleep apnea [article]. Otolaryngology—head and neck surgery, vol. 143, No. 4, pp. 585-590. IP: 128.210.125.135. Jun. 10, 2010. SAGE.

Woodson et al. Response to: Multicenter study of a novel adjustable tongue-advacement device for obstructive sleep apnea [article]. Otolaryngology—head and neck surgery, vol. 144, No. 6, pp. 1009-1012. 2011. SAGE.

Siesta Medical. Siesta Medical receives 510(k) clearance for Encore system to treat obstructive sleep apnea [press release]. Sep. 12, 2011. pp. 1-2.

Aspire Medical, Inc. Aspire Medical announces first implant in US and start of clinical trial to treat sleep apnea [article]. Medical News Today. May 23, 2007. pp. 1-4. URL: <http://www.medicalnewstoday.com/releases/71787.php>.

Hamans et al. A novel tongue implant for tongue advancement for obstructive sleep apnea: feasibility, safety and histology in a canine model [article]. J Musculoskelet Neuronal Interact. vol. 10, No. 1, pp. 100-111. Dec. 29, 2009. Hylonome.

Knobbe, Martens, Olson & Bear, LLP. Amendment and response to non-Final Office Action dated Jan. 18, 2013, for U.S. Appl. No. 13/077,813, filed Mar. 31, 2011. First Named Inventor, van der Burg. Title, Suture Passer Systems and Methods for Tongue or Other Tissue Suspension and Compression.

PR Newswire. Asprie Medical appoints Roseanne Varner as president and CEO [press release]. pp. 1-2. May 1, 2011. URL: <http://www.prnewswire.com/news-releases/aspire-medical-appoints-roseanne-varner-as-president-and-ceo-57760852.html>.

Park. Aspire Medical Advance System for obstructive sleep apnea [blog]. Dr. Park: Breathe better, sleep better, live better. pp. 1-4. Oct. 6, 2010. URL: <http://doctorstevenpark.com/aspire-medical-advance-system-for-obstructive-sleep-apnea>.

Revent Medical. The Revent Solution: Tongue Implanter Kit [webpage]. 2014. pp. 1-2. Retrieved Aug. 12, 2014. URL: <http://www.reventmedical.com/solution/>.

Revent Medical. The Revent Solution: Implants [webpage]. 2014. pp. 1-2. Retrieved Aug. 12, 2014. URL: <www.reventmedical.com/solution/>.

International Searching Authority, International Search Report and Written Opinion for International application No. PCT/US2014/049341, dated Nov. 19, 2014, pp. 1-11.

File history of U.S. Appl. No. 08/883,220, now U.S. Pat. No. 5,988,171, as of Nov. 21, 2013. Filing date, Jun. 26, 1997. First Named Inventor, Ze'ev Sohn. Title, Methods and Devices for the Treatment of Airway Obstruction, Sleep Apnea and Snoring.

File history of U.S. Appl. No. 10/877,003, now U.S. Pat. No. 7,213,599, as of Nov. 21, 2013. Filing date, Jun. 24, 2004. First Named Inventor, Timothy R. Conrad. Title, Airway Implant.

File history of U.S. Appl. No. 11/757,501, now U.S. Pat. No. 7,703,460, as of Nov. 21, 2013. Filing date, Jun. 4, 2007. First Named Inventor, Timothy R. Conrad. Title, Tongue Implant.

File history of U.S. Appl. No. 12/214,084 as of Nov. 21, 2013. Filing date, Jun. 17, 2008. First Named Inventor, Octavian Iancea. Title, Implantable devices, systems, and methods for maintaining desired orientations in targeted tissue regions.

European Patent Office, "Extended European Search Report," for Intl. App. No. 16150647.2, dated Apr. 12, 2016, pp. 1-7.

* cited by examiner

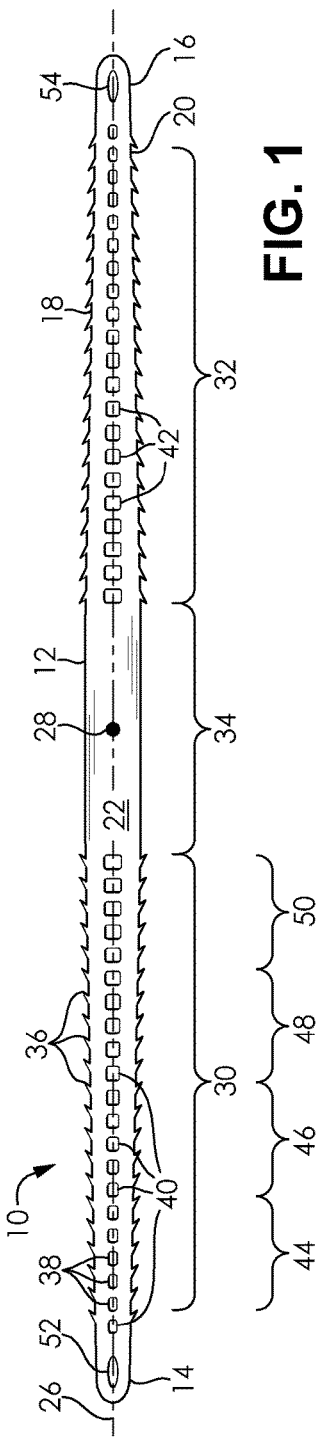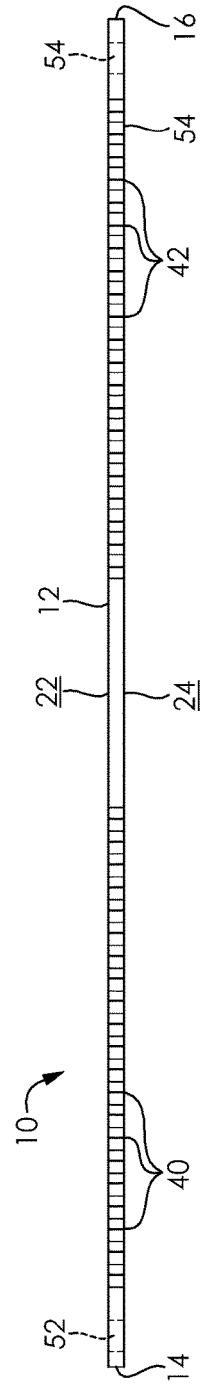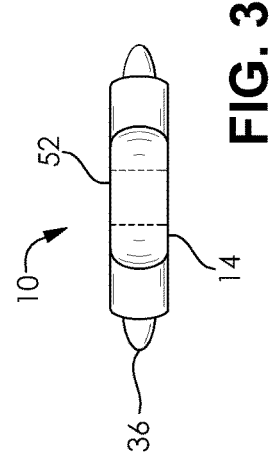

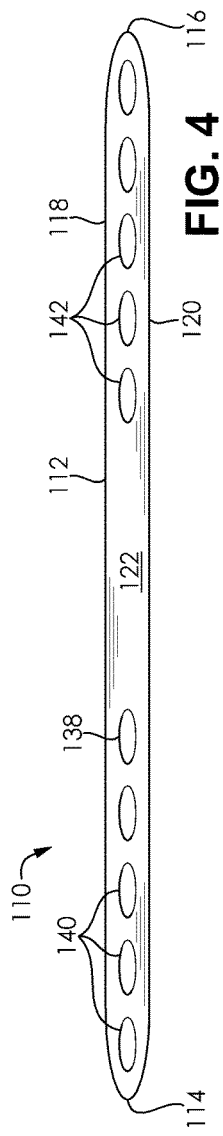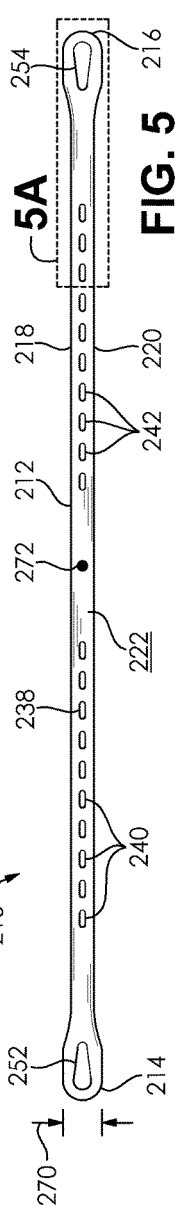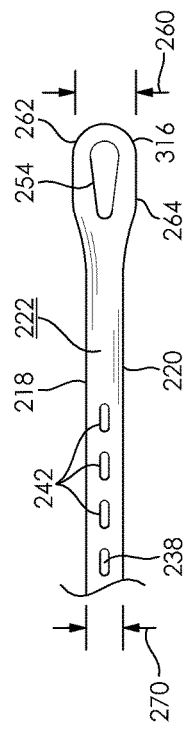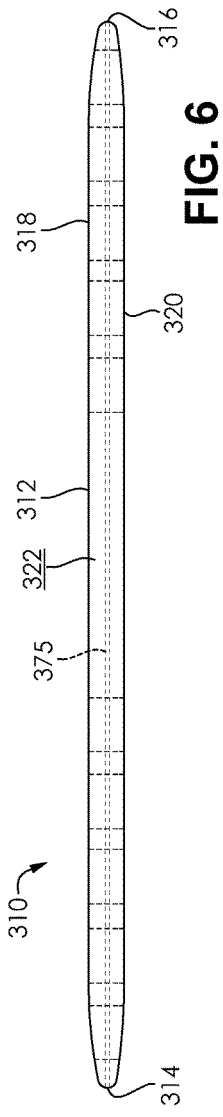

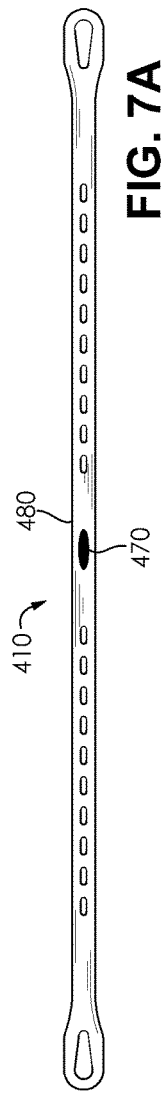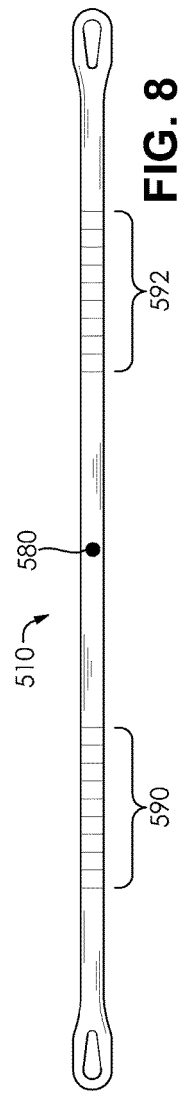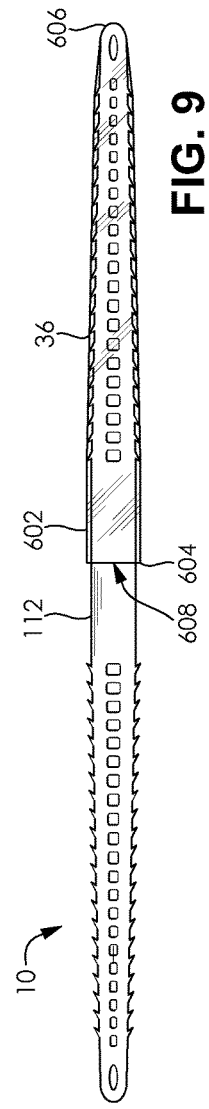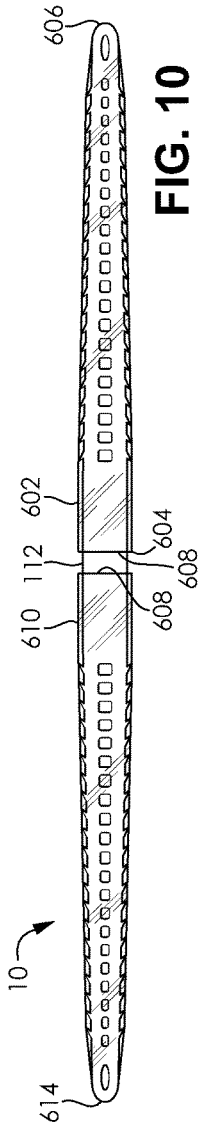

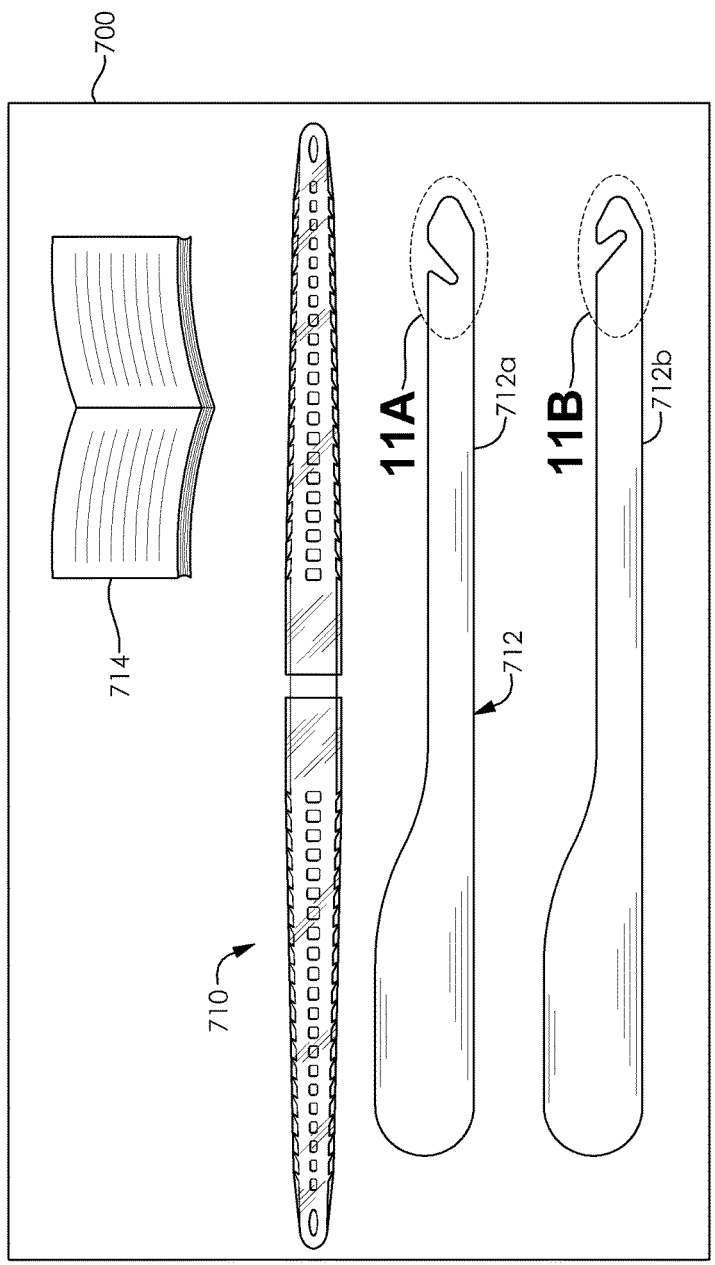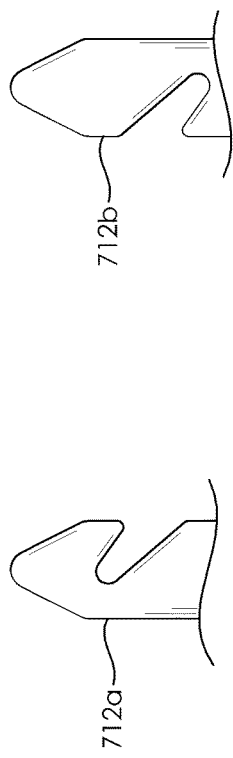

SLING-BASED TREATMENT OF OBSTRUCTIVE SLEEP APNEA

FIELD

The disclosure relates generally to the field of implantable medical devices. More particularly, the disclosure relates to sling devices for securement of tissue within the body. The devices described herein are useful in the treatment of Obstructive Sleep Apnea. The disclosure also relates to kits that include a sling device, and methods of treatment in which a sling device is used.

BACKGROUND

It is sometimes necessary or desirable to secure a tissue or portion of a tissue within the body of an animal, such as a human. Sling devices are known in the art and can be used to affect such a securement of tissue within the body.

Obstructive Sleep Apnea (OSA) is a clinical disorder in which a partial or complete collapse of soft tissue occurs in the airway during sleep. This leads to a blockage of the airway and impaired breathing during sleep. Mild OSA can lead to fatigue, reduced alertness following sleep, and a general reduction in productivity for the affected individual. Severe OSA can lead to sleep deprivation, hypoxemia, and depression.

OSA can be the result of obesity and/or diabetes. It is believed that about 1 in every 15 Americans are affected by some form of OSA, leading to an estimated $3.4 billion in associated healthcare costs each year.

The art provides various options for the treatment of OSA. Continuous Positive Airway Pressure (CPAP) machines, which supply positive air pressure through a facemask and into the airway during sleep, are used most frequently. The positive air pressure maintains an open airway to prevent apnea and snoring. While these machines are generally considered effective, they are bulky, noisy, and cumbersome to use. Furthermore, use of these machines can be socially awkward for some individuals.

Oral appliances that force the jaw forward to maintain an open airway can also be used. These devices are generally considered to be not as effective as CPAP machines, and can be uncomfortable to use. Furthermore, these devices are frequently ejected from the mouth during sleep, reducing their effectiveness over the entire course of a sleeping period.

Invasive surgical procedures can also be used to treat OSA. Various techniques have been described, including uvulopalatopharyngoplasty (UPP, maxillomandibular advancement (MMA), and even tracheostomy. Surgical procedures are generally considered to have limited and potentially short-lived effectiveness. Furthermore, many of the procedures require hospitalization and the use of general anesthesia. As a result, these procedures are generally reserved for severe cases of OSA.

The Repose™ System from Medtronic provides a surgical-based tongue suspension procedure that can be performed with or without an adjunct hyoid suspension procedure. These suspension procedures require a surgical incision and dissection of the neck below the mandible. Following implantation of one or more necessary bone screws, sutures are lashed around the tongue and/or hyoid bone and secured with surgical knots. While these procedures offer less complicated solutions than the surgical procedures above, they still require surgical intervention and suffer from the drawbacks associated with surgical procedures. Furthermore, over time, the sutures used to suspend the tongue and/or hyoid bone may weaken or even snap, which may limit the effectiveness of the treatment over time. Lastly, the use of sutures in these procedures necessitates the use of specialized knotting and securement techniques to complete the procedure, which adds an additional opportunity for error and failure in the device and the procedure.

Considering the disadvantages of the various available treatment options described above, a need exists for improved devices for securement of tissue within the body. Furthermore, a need exists for additional options, including devices, kits and methods, for the treatment of OSA.

BRIEF SUMMARY OF DESCRIBED EMBODIMENTS

Various exemplary sling devices are described and illustrated herein.

An exemplary sling device comprises a main body extending along a lengthwise axis and having first and second opposing ends, first and second opposing sides, and first and second opposing surfaces; a first ribbed portion extending along the lengthwise axis from a first point disposed on the lengthwise axis between a longitudinal midpoint and the first end to a second point disposed on the lengthwise axis between the longitudinal midpoint and the first end; a second ribbed portion extending along the lengthwise axis from a third point disposed on the lengthwise axis between the longitudinal midpoint and the second end to a second point disposed on the lengthwise axis between the longitudinal midpoint and the second end; and a non-ribbed middle portion extending along the lengthwise axis across the longitudinal midpoint from an end of the first ribbed portion to an end of the second ribbed portion.

Various kits are described and illustrated herein.

An exemplary kit comprises a sling and one or more needles adapted to engage the sling.

Various methods of treatment are described herein.

An exemplary method comprises creating two openings in the mandible of a patient; creating a transverse passageway in the tongue of the patient such that the passageway lies on a plane that is transverse to the longitudinal axis of the tongue; advancing a device through one of the two openings in the mandible and through the tongue of the patient; advancing a second device through the other of the two openings in the mandible and through the tongue of the patient; engaging a sling according to an embodiment with a device disposed through the transverse passageway in the tongue; pulling the device and attached sling through the transverse passageway in the tongue until the sling is disposed in the transverse passageway; engaging the sling with the first device such that a pulling force applied to the first device will result in a first end of the sling being pulled along with the first device through the tongue and through first opening in the mandible; engaging the sling with the second device such that a pulling force applied to the second device will result in a second end of the sling being pulled along with the second device through the tongue and the second opening in the mandible; pulling the first and second devices and the first and second ends of the sling through the respective openings in the mandible until each end of the sling has exited the respective opening; pulling the tongue toward the front of the mouth or mandible; and securing the sling to a tissue to support the tongue in the new position.

Additional understanding of these exemplary devices, kits and methods can be obtained with review of the detailed description, below, and the appended drawings.

BRIEF DESCRIPTION OF THE DRAWINGS

FIG. 1 is a perspective view of a first exemplary sling device.

FIG. 2 is an elevation view of the sling device illustrated in FIG. 1.

FIG. 3 is an end view of the sling device illustrated in FIG. 1.

FIG. 4 is a perspective view of a second exemplary sling device.

FIG. 5 is a perspective view of a third exemplary sling device.

FIG. 5A is a magnified view of area I in FIG. 5.

FIG. 6 is a perspective view of a fourth exemplary sling device.

FIG. 7A is a perspective view of another exemplary sling device.

FIG. 7B is a perspective view of another exemplary sling device.

FIG. 8 is a perspective view of another exemplary sling device.

FIG. 9 is a perspective view of the sling device illustrated in FIG. 1 disposed within a sheath.

FIG. 10 is a perspective view of the sling device illustrated in FIG. 1 disposed within first and second sheaths.

FIG. 11 is a schematic illustration of an exemplary kit.

FIG. 11A is a magnified view of the distal end of a first needle of the kit illustrated in FIG. 11.

FIG. 11B is a magnified view of the distal end of a second needle of the kit illustrated in FIG. 11.

DETAILED DESCRIPTION OF DESCRIBED EMBODIMENTS

Figure 12:
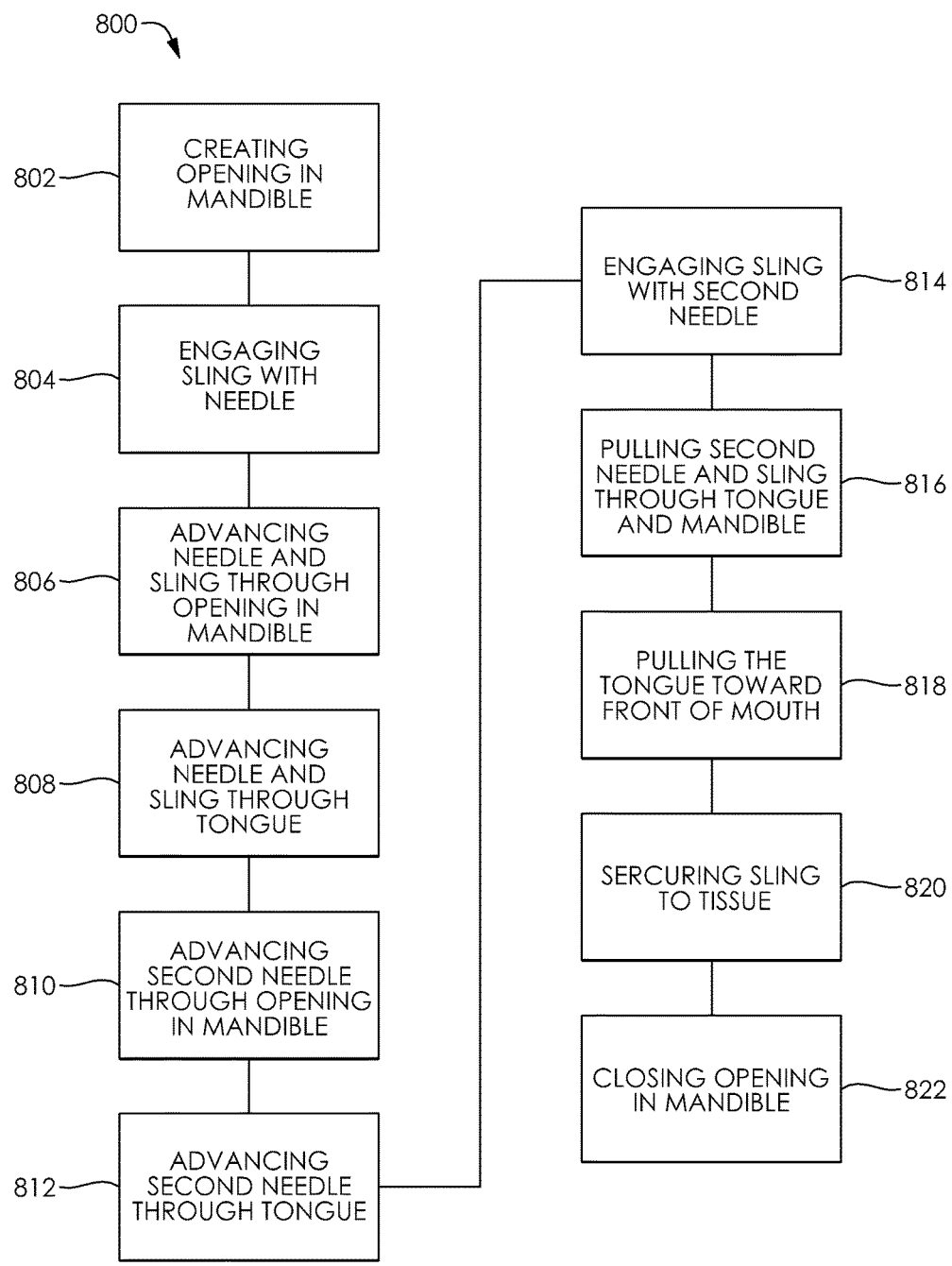
FIG. 12 is a flowchart illustration of a first exemplary method of treatment.

The following detailed description and the appended drawings describe and illustrate various exemplary devices, kits and methods. The description and drawings are exemplary in nature and are provided to enable one skilled in the art to make and use one or more exemplary device and/or to practice one or more exemplary method. They are not intended to limit the scope of the claims in any manner.

FIGS. 1 through 3 illustrate a first exemplary sling 10. The sling 10 has a main body 12 comprising a substantially flat member extending from a first end 14 to an opposing second end 16 and having first 18 and second 20 opposing sides. The main body 12 has a first 22 or upper surface and an opposing second 24 or lower surface.

As best illustrated in FIG. 1, the main body 12 has a lengthwise axis 26 and a longitudinal midpoint 28 disposed on the lengthwise axis. A first ribbed portion 30 extends along the lengthwise axis 26 of the main body 12 from a point on the lengthwise axis 26 between the longitudinal midpoint 28 and the first end 14 to another point on the lengthwise axis 26 between the longitudinal midpoint 28 and the first end 14. Similarly, a second ribbed portion 32 extends along the lengthwise axis 26 of the main body 12 from a point on the lengthwise axis 26 between the longitudinal midpoint 28 and the second end 16 to another point on the lengthwise axis 26 between the longitudinal midpoint 28 and the second end 16. A non-ribbed middle portion 34 extends along the lengthwise axis 26 of the main body 12 across the longitudinal midpoint 28 from an end of the first ribbed portion 30 to an end of the second ribbed portion 32.

Each of the ribbed portions 32, 34 includes a series of ribs 36 that extend outwardly from the respective side 18, 20, away from the longitudinal axis 26. As best illustrated in FIG. 1, each rib 36 advantageously extends away from the respective side 18, 20 at a non-orthogonal angle with respect to the lengthwise axis 26. Furthermore, each rib 36 advantageously extends away from the respective side 18, 20 at an acute angle with respect to the longitudinal midpoint 28 on the lengthwise axis 26.

As used herein, the term "rib" refers to an outwardly-directed protrusion extending from a surface. An individual rib can have any suitable shape, including regular and irregular shapes, symmetrical and asymmetrical shapes, and any other suitable shape. The term "series of ribs" refers to two or more individual ribs. A series of ribs includes multiple ribs having the same shape, size and or/configurations, a series of ribs having different sizes, shapes and configurations, a series of ribs spaced at regular intervals, such as a toothed surface, a series of ribs spaced at different intervals, and a series of ribs spaced at irregular intervals. Examples of suitable configurations for ribs include one in which ribs extend toward an end of the sling and one in which ribs extend toward the center of the sling.

Inclusion of the ribs 36 is considered advantageous at least because the outwardly-projecting structure of the rib provides additional surface area beyond that of the respective side 18, 20 for contacting and/or engaging with tissue within the body. This additional surface area is expected to enhance the anchoring of the sling in the body as a result of the additional contact formed between the sling and tissue. The ribs 36 are considered particularly advantageous in slings formed of remodellable material, as described more fully below.

The main body 12 defines a plurality of openings 38 that extend through the thickness of the main body 12 from the first surface 22 to the second surface 24. As such, each opening 38 defines a passageway that extends through the main body. As best illustrated in FIG. 1, a first series 40 of openings 38 is disposed on the first ribbed portion 30, and a second series 42 of openings 38 is disposed on the second ribbed portion 32. Each series 40, 42 of openings 38 advantageously includes multiple sets of openings 38 of identical dimensions. Advantageously, the openings 38 of one set have different dimensions from the openings of all other sets in the series 40, 42. For example, as best illustrated in FIG. 1, each series 40, 42 of openings 38 includes four sets 44, 46, 48, 50 of openings 38. The openings 38 of each set have dimensions that are identical with those of the other openings 38 in the set, but that are different from those of the other sets.

It is noted that the openings of one set can have one or more dimensions that differ from the same dimension or dimensions of openings of another set while also have one or more dimension that is the same or substantially similar to the same dimension or dimensions of the openings of the other set. For example, each opening of one set may have a rectangular shape having a length and width that differ from the length and width of a rectangular-shaped opening of another set, but the two openings may have the same overall area and/or perimeter length. As described below, the main body is advantageously formed of a bioremodellable material. Inclusion of multiple series of openings having different dimensions while having the same or substantially similar overall area and/or perimeter length is believed to provide a desirable amount of surface area that can may aid in efficient A first end opening 52 is disposed at the first end 14 of the main body 12 and extends through the thickness of the main body 12 from the first surface 22 to the second surface 24. Similarly, a second end opening 54 is disposed at the second end 16 of the main body 12 and extends through the thickness of the main body 12 from the first surface 22 to the second surface 24. As such, each end opening 52, 54 defines a passageway that extends through the main body 12.

As best illustrated in FIG. 2, the first 22 and second 24 surfaces of the main body 12 are substantially flat. It is noted, though, that it may be advantages to include one or more bumps, projections or other surface modifications on one or both of the surfaces 22, 24. Inclusion of such modifications may improve the handling of the sling 10 during use.

The sling 10 can be formed of any suitable material, and a skilled artisan will be able to select an appropriate material for a sling according to a particular embodiment based on various considerations, including the tissue with which the sling is intended to be used, the technique by which the sling will be implanted, and other considerations. Both synthetic and natural materials are considered suitable. Examples of suitable synthetic materials include polymeric materials, such as polyethylene, polypropylene and other flexible polymeric materials. Examples of suitable natural materials include tissue and tissue-derived materials. The inventors have determined that slings formed of bioremodellable materials are particularly well-suited for securement of various tissues in human and other animals at least because of the ability of such materials to remodel and become incorporated into adjacent tissues over time. These materials can provide a scaffold onto which cellular in-growth can occur, eventually allowing the material to remodel into a structure of host cells, which aids in the effectiveness of the sling as a long-term support of the tissue being secured.

Particular advantage can be provided by slings that incorporate a remodelable collagenous material. Such remodelable collagenous materials, whether reconstituted or naturally-derived, can be provided, for example, by collagenous materials isolated from a warm-blooded vertebrate, especially a mammal. Such isolated collagenous material can be processed so as to have remodelable, angiogenic properties and promote cellular invasion and ingrowth. Remodelable materials may be used in this context to stimulate ingrowth of adjacent tissues into an implanted construct such that the remodelable material gradually breaks down and becomes replaced by new patient tissue so as to generate a new, remodeled tissue structure.

Suitable remodelable materials can be provided by collagenous extracellular matrix (ECM) materials possessing biotropic properties. For example, suitable collagenous materials include ECM materials such as those comprising submucosa, renal capsule membrane, dermal collagen, dura mater, pericardium, fascia lata, serosa, peritoneum or basement membrane layers, including liver basement membrane. Suitable submucosa materials for these purposes include, for instance, intestinal submucosa including small intestinal submucosa, stomach submucosa, urinary bladder submucosa, and uterine submucosa. Collagenous matrices comprising submucosa (potentially along with other associated tissues) useful in the present invention can be obtained by harvesting such tissue sources and delaminating the submucosa-containing matrix from smooth muscle layers, mucosal layers, and/or other layers occurring in the tissue source. For additional information as to some of the materials useful in the present invention, and their isolation and treatment, reference can be made, for example, to U.S. Pat. Nos. 4,902,508, 5,554,389, 5,993,844, 6,206,931, and 6,099,567.

Remodelable ECM tissue materials harvested as intact sheets from a mammalian source and processed to remove cellular debris advantageously retain at least a portion of and potentially all of the native collagen microarchitecture of the source extracellular matrix. This matrix of collagen fibers provides a scaffold to facilitate and support tissue ingrowth, particularly in bioactive ECM implant materials, such as porcine small intestinal submucosa or SIS (Surgisis® Biodesign™, Cook Medical, Bloomington Ind.), that are processed to retain an effective level of growth factors and other bioactive constituents from the source tissue. In this regard, when a sling incorporates this sort of material, cells will invade the remodelable material upon implantation eventually leading to the generation of a newly-remodeled, functional tissue structure.

Submucosa-containing or other ECM tissue used in the slings is preferably highly purified, for example, as described in U.S. Pat. No. 6,206,931 to Cook et al. Thus, preferred ECM material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 µg/mg, more preferably less than about 2 µg/mg, and virus levels are preferably less than about 50 plaque forming units (PFU) per gram, more preferably less than about 5 PFU per gram. These and additional properties of submucosa or other ECM tissue taught in U.S. Pat. No. 6,206,931 may be characteristic of any ECM tissue used in the inventive slings.

A typical layer thickness for an as-isolated submucosa or other ECM tissue layer used in the invention ranges from about 50 to about 250 microns when fully hydrated, more typically from about 50 to about 200 microns when fully hydrated, although isolated layers having other thicknesses may also be obtained and used. These layer thicknesses may vary with the type and age of the animal used as the tissue source. As well, these layer thicknesses may vary with the source of the tissue obtained from the animal source. In a dry state, a typical layer thickness for an as-isolated submucosa or other ECM tissue layer used in the invention ranges from about 30 to about 160 microns when fully dry, more typically from about 30 to about 130 microns when fully dry.

Suitable bioactive agents may include one or more bioactive agents native to the source of the ECM tissue material. For example, a submucosa or other remodelable ECM tissue material may retain one or more growth factors such as but not limited to basic fibroblast growth factor (FGF-2), transforming growth factor beta (TGF-beta), epidermal growth factor (EGF), cartilage derived growth factor (CDGF), and/or platelet derived growth factor (PDGF). As well, submucosa or other ECM materials when used in the invention may retain other native bioactive agents such as but not limited to proteins, glycoproteins, proteoglycans, and glycosaminoglycans. For example, ECM materials may include heparin, heparin sulfate, hyaluronic acid, fibronectin, cytokines, and the like. Thus, generally speaking, a submucosa or other ECM material may retain one or more bioactive components that induce, directly or indirectly, a cellular response such as a change in cell morphology, proliferation, growth, protein or gene expression.

Submucosa-containing or other ECM materials used in a sling can be derived from any suitable organ or other tissue source, usually sources containing connective tissues. The ECM materials processed for use in the inventive slings will typically include abundant collagen, most commonly being constituted at least about 80% by weight collagen on a dry weight basis. Such naturally-derived ECM materials will for the most part include collagen fibers that are non-randomly oriented, for instance occurring as generally uniaxial or multi-axial but regularly oriented fibers. When processed to retain native bioactive factors, the ECM material can retain these factors interspersed as solids between, upon and/or within the collagen fibers. Particularly desirable naturally-derived ECM materials for use in the invention will include significant amounts of such interspersed, non-collagenous solids that are readily ascertainable under light microscopic examination with appropriate staining. Such non-collagenous solids can constitute a significant percentage of the dry weight of the ECM material in certain inventive embodiments, for example at least about 1%, at least about 3%, and at least about 5% by weight in various embodiments of the invention.

The submucosa-containing or other ECM material used in the inventive slings may also exhibit an angiogenic character and thus be effective to induce angiogenesis in a host engrafted with the material. In this regard, angiogenesis is the process through which the body makes new blood vessels to generate increased blood supply to tissues. Thus, angiogenic materials, when contacted with host tissues, promote or encourage the formation of new blood vessels into the materials. Methods for measuring in vivo angiogenesis in response to biomaterial implantation have recently been developed. For example, one such method uses a subcutaneous implant model to determine the angiogenic character of a material. See, C. Heeschen et al., Nature Medicine 7 (2001), No. 7, 833-839. When combined with a fluorescence microangiography technique, this model can provide both quantitative and qualitative measures of angiogenesis into biomaterials. C. Johnson et al., Circulation Research 94 (2004), No. 2, 262-268.

Further, in addition or as an alternative to the inclusion of such native bioactive components, non-native bioactive components such as those synthetically produced by recombinant technology or other methods (e.g., genetic material such as DNA), may be incorporated into an ECM material used in an inventive sling. These non-native bioactive components may be naturally-derived or recombinantly produced proteins that correspond to those natively occurring in an ECM tissue, but perhaps of a different species. These non-native bioactive components may also be drug substances. Illustrative drug substances that may be added to materials include, for example, anti-clotting agents, e.g. heparin, antibiotics, anti-inflammatory agents, thrombus-promoting substances such as blood clotting factors, e.g., thrombin, fibrinogen, and the like, and anti-proliferative agents, e.g. taxol derivatives such as paclitaxel. Such non-native bioactive components can be incorporated into and/or onto ECM material in any suitable manner, for example, by surface treatment (e.g., spraying) and/or impregnation (e.g., soaking), to name a few. Also, these substances may be applied to the ECM material in a premanufacturing step, immediately prior to the procedure (e.g., by soaking the material in a solution containing a suitable antibiotic such as cefazolin), or during or after engraftment of the material in the patient.

Inventive devices can incorporate xenograft material (i.e., cross-species material, such as tissue material from a non-human donor to a human recipient), allograft material (i.e., interspecies material, with tissue material from a donor of the same species as the recipient), and/or autograft material (i.e., where the donor and the recipient are the same individual). Further, any exogenous bioactive substances incorporated into an ECM material may be from the same species of animal from which the ECM material was derived (e.g. autologous or allogenic relative to the ECM material) or may be from a different species from the ECM material source (xenogenic relative to the ECM material). In certain embodiments, ECM material will be xenogenic relative to the patient receiving the graft, and any added exogenous material(s) will be from the same species (e.g. autologous or allogenic) as the patient receiving the graft. Illustratively, human patients may be treated with xenogenic ECM materials (e.g. porcine-, bovine- or ovine-derived) that have been modified with exogenous human material(s) as described herein, those exogenous materials being naturally derived and/or recombinantly produced.

The inventors have determined that SIS is particularly well-suited for use in the sling devices described herein at least because of its well-characterized nature and ready availability. Furthermore, the inventors have determined that vacuum-pressed SIS provides a particularly advantageous material from which to form sling devices that include one or more series of ribs, such as the sling 10 described above and illustrated in FIGS. 1 through 3. Lyophilized SIS can also be used, and may be advantageous for slings in which a relatively quicker remodeling time is desired. Radiopaque SIS can also be used, and may be advantageous for slings for which enhanced visualization characteristics are desired.

The inventors have determined that a sling having a main body formed of multiple layers laminated together provides a particularly advantageous structure. Thus, the main body can comprise a multilaminate construct. In these embodiments, any suitable number of layers can be used, and a skilled artisan will be able to select an appropriate number of layers for a particular sling based on various considerations, including the intended use of the sling and nature of the tissue intended to be supported by the sling. The inventors have determined that a sling having a main body formed of between 4 and 12 layers of an ECM material, such as SIS, provides a particularly advantageous structure for slings intended for use in supporting the tongue of a patient, such as in methods of treating OSA. A main body formed of between 6 and 10 layers of an ECM material, such as SIS, is also considered particularly advantageous. A main body formed of 8 layers of an ECM material, such as SIS, is also considered particularly advantageous. In these embodiments, the layers can be assembled together in any suitable manner and using any suitable technique or process. For multilaminate SIS constructs, the inventors have determined that vacuum-pressing of multiple layers of SIS provides a suitable laminate structure for use as a sling as described herein.

The inventors have determined that a hybrid structure may provide a desirable balance between desired overall rigidity for the sling and relative remodeling time. In this embodiment, a middle portion of the sling is formed of lyophilized SIS, which provides a relatively quicker remodeling time, and the perimeter sections, including the ribbed portions, are formed of vacuum-pressed SIS, which provides a relatively high degree of overall rigidity. The middle portion in this embodiment is expected to remodel relatively quickly following implantation, enhancing the securement of the sling. An opposite structure is also considered suitable and may be advantageous in certain circumstances.

A hybrid structure in which a mesh is embedded inside an SIS or other composition or between layers of SIS or of other material is also considered suitable. For example, a polymeric mesh, such as a mesh formed of polypropylene, can be disposed between layers of SIS during formation of the sling. In these embodiments, the polymeric mesh will remain in the body following completion of remodeling by the SIS, which may enhance the overall anchoring of the supported tissue over time. A bioabsorable mesh, such as a mesh formed of polyglycolic acid or other bioabsorbable material, can also be included in the sling in this manner and may be advantageous where supplemental support is desired that lasts beyond the remodeling time for the SIS, but that does not have the permanency associated with a polypropylene or other polymeric mesh. Examples of suitable structural arrangements of polymer and remodelable layers can be found in United States Patent Application Publication No. 2011/0166673 to Patel et al., for QUILTED IMPLANTABLE GRAFT, the entire contents of which are hereby incorporated into this disclosure.

FIG. 4 illustrates another exemplary sling 110. The sling 110 of this embodiment is similar to the embodiment described above and illustrated in FIGS. 1 through 3, except as described below. Thus, the sling 110 includes a main body 112 having first 114 and second 116 opposing ends, first 118 and second 120 opposing sides, and first 122 and second (not illustrated in FIG. 2) opposing surfaces. The sling includes first 140 and second 142 series of openings 138.

In this embodiment, the sides 118, 120 are substantially flat surfaces. Thus, in contrast to the embodiment illustrated in FIGS. 1 through 3, the sling 110 does not include any outwardly-projecting ribs. Furthermore, the sides 118, 120 are substantially parallel to each other along substantially the entire length of the sling 110. Also, each of the openings 138 are substantially similar in all dimensions.

FIGS. 5 and 5A illustrate another exemplary sling 210. The sling 210 of this embodiment is similar to the embodiment described above and illustrated in FIGS. 1 through 3, except as described below. Thus, the sling 210 includes a main body 212 having first 214 and second 216 opposing ends, first 218 and second 220 opposing sides, and first 222 and second (not illustrated in FIG. 5 or 5A) opposing surfaces. The sling 210 includes first 240 and second 242 series of openings 238.

Similar to the embodiment illustrated in FIG. 4, the sides 218, 220 are substantially flat surfaces. Thus, in contrast to the embodiment illustrated in FIGS. 1 through 3, the sling 210 does not include any outwardly-projecting ribs. Also, each of the openings 238 has an ovoid or substantially ovoid shape and all openings 238 are substantially similar in all dimensions.

The first 214 end defines a first end loop 252 and the second end 216 defines a second end loop 254. The first end loop 252 is disposed at the first end 214 of the main body 212 and extends through the thickness of the main body 212 from the first surface 222 to the second surface. Similarly, the second end loop 254 is disposed at the second end 216 of the main body 212 and extends through the thickness of the main body 212 from the first surface 222 to the second surface. As such, each end loop 252, 254 defines a passageway that extends through the main body 212. It is noted that while the illustrated sling 210 includes a loop at each end, a sling can include a single loop at one end and a closed end or differently-formed loop at the other end. For example, a sling can include an end loop at one end, such as first end loop 252, and a structure similar to any end from any embodiment described herein at the opposite end.

In contrast to the first 52 and second 54 end openings of the first exemplary sling 10, best illustrated in FIGS. 1 and 2, each of the first 252 and second 254 end loops of this embodiment have a width 260 extending from a first lateral side 262 to an opposing second lateral side 264 of the sling 210 and along an axis orthogonal to a lengthwise axis of the sling 210 that is greater than a width 270 extending from a first lateral side 218 to an opposing second lateral side 220 of the sling 210 and along an axis that intersects a midpoint 272 of and is orthogonal to a lengthwise axis of the sling 210. This structure is considered advantageous at least because it facilitates handling of the first 214 and second 216 ends of the sling 210 during use and also allows each of the first end loop 252 and second end loop 254 to define a larger opening, which facilitates engagement of the sling 210 with various tools that can be used during placement around or through the tissue to be secured, such as the tongue in the methods described in detail below.

A sling according to a particular embodiment can have any suitable dimensions and a skilled artisan will be able to select appropriate dimensions for a particular sling based on various considerations, including the nature, location of and route of access to the tissue to be secured by the sling. The inventors have determined that a sling intended to secure the tongue to the mandible in accordance with a method described herein advantageously has a length that is between about 25 cm and about 35 cm, a width at the longitudinal midpoint that is between about 4 mm and about 8 mm, widths at the ends that are between about 7 mm and about 11 mm—the two ends having the same or different widths, an opening length that is between about 2 mm and about 3 mm, and an end loop opening length that is between about 2 mm and about 6 mm.

A sling according to an embodiment of the invention, such as the various embodiments described and illustrated herein or other embodiments, can include various additional properties, elements and/or associated devices that facilitate the use of a particular sling in a particular method, such as any of the exemplary methods of treatment described in detail below. For example, a sling can include a structure, such as an embedded wire or other stiffening member, to facilitate handling and/or securement of the sling; one or more radiopaque markers to facilitate visualization of the sling before, during or after placement; external or other indicia that aid in the use of the sling; and/or one or more sheaths to protect the sheath and/or to enhance the ability of the sling to pass through passages within tissue, such as a tongue, during use. Various examples of slings according to such embodiments are described below.

FIG. 6 illustrates another exemplary sling 310. The sling 310 of this embodiment is similar to the embodiment described above and illustrated in FIGS. 1 through 3, except as described below. Thus, the sling 310 includes a main body 312 having first 314 and second 316 opposing ends, first 318 and second 320 opposing sides, and first 322 and second (not illustrated in FIG. 2) opposing surfaces.

In this embodiment, the sides 318, 320 are substantially flat surfaces. Thus, in contrast to the embodiment illustrated in FIGS. 1 through 3, the sling 310 does not include any outwardly-projecting ribs. Also, the sling 310 does not include any openings extending through the thickness of the main body 312.

An elongate wire member 375 is disposed within the main body 312 and extends substantially along the length of the main body 312 from the first end 314 to the second end 316. Inclusion of the elongate wire member 375 confers radiopacity onto the sling, which facilitates imaging of the sling 310 following implantation using appropriate imaging equipment and techniques, such as fluoroscopy. Furthermore, the type, size and configuration of the elongate wire member can be selected to enhance the rigidity and/or pushability of the sling 310 and aid in the handling and implantation of the sling 310, if desired.

If included, the elongate wire member 375 can be formed of any suitable material, and a skilled artisan will be able to select an appropriate material based on various considerations, including the desired rigidity of the wire member and any visualization concerns and/or needs. Stainless steel is considered particularly well-suited for the wire member at least because of its well-characterized nature, ready availability, and its advantageous rigidity and imaging properties. Any other suitable material can be used, including other metals, polymeric materials, and any other material now known or hereinafter developed. Gold, platinum and other dense metals can be used for the elongate wire member in slings for which imaging is critical or expected to be challenging.

For slings in which an elongate wire member 375 is included, the inventors have determined that vacuum-pressed remodellable material, such as vacuum-pressed SIS, provides a suitable material for forming the main body of the sling while facilitating placement of the elongate wire member within the main body.

It is noted that while the elongate wire member is described and illustrated as extending substantially along the length of the main body 312 from the first end 314 to the second end 316, any suitable length can be used, including a length that is between 25 and 100% of the entire length of the sling 310, a length that is between 50 and 100% of the entire length of the sling 310, a length that is between 75 and 100% of the entire length of the sling 310, a length that is between 85 and 100% of the entire length of the sling 310, and a length that is between 95 and 100% of the entire length of the sling 310.

Furthermore, while the elongate wire member 375 is described and illustrated as having a substantially linear configuration, any suitable shape and/or configuration can be used. Also, while the elongate wire member 375 is described and illustrated as being entirely contained within the sling 310, a portion or portions of the elongate wire member 375 can extend through and out of the sling 310 to facilitate removal from the sling 310 following implantation, as described below.

It is also noted that while a single elongate wire member is described and illustrated, the inventors have determined that it may be desirable to include multiple wire members in slings according to particular embodiments. For example, two elongate wire members positioned side-by-side may be included if the ability to discern particular orientations of the sling under visualization is desired.

As noted above, inclusion of the elongate wire member 375 enhances the imaging characteristics of the sling 310 by providing a radiopaque body that can be visualized using appropriate equipment and techniques. A sling can be modified to include appropriate structure and/or additional elements to enhance its imaging characteristics using alternative imaging techniques, if desired. For example, a sling can be rendered echogeneic by introducing dimples onto a surface of a sling, by including beads or other structures on the surface of a sling or embedded within the sling, by including bubbles in the material of the sling, or by using other appropriate structures and/or elements. A sling modified in this way can be visualized using ultrasound equipment and techniques, which may be desirable in situations in which it is either not possible or undesirable to use x-rays.

Other types and forms of markers can be used as well. For example, as illustrated in FIG. 7A, a sling 410 can include a radiopaque marker 470 positioned at a longitudinal midpoint 480 of the sling 410. This configuration is considered advantageous at least because it facilitates visualization of the midpoint 480 of the sling 410 during placement, which can aid in placing the sling across a midpoint of a targeted tissue, such as the tongue.

Alternatively, as illustrated in FIG. 7B, a sling 410' can include two radiopaque markers 472, 474 positioned on a longitudinal axis of the sling 410' and separated by a predetermined distance. A clinician can use markers 472, 474 positioned in this configuration to verify that the markers 472, 474 lie in a straight or substantially straight line, which can be indicative of a placement in which the sling 410' or portion of the sling 410' has not rolled onto itself or adopted any other undesirable configuration prior to a final placement or securement.

Indeed, any suitable number, configuration and arrangement of radiopaque markers can be included in a sling according to a particular embodiment and a skilled artisan will be able to construct a sling with an appropriate number, configuration and arrangement of such markers based on various considerations, including the nature of the material from which the sling is comprised, the intended use of the sling, and any desired visualization techniques, methods and/or equipment with which the sling is intended to be used.

Furthermore, it is noted that, in any embodiment in which one or more radiopaque marker is included, the marker or markers can be formed of any suitable material, and a skilled artisan will be able to select an appropriate material based on various considerations, including any visualization concerns and/or needs. Gold, platinum and other dense metals are considered suitable for this purpose.

In addition to radiopaque markers, different types and forms of indicia can be used as well. For example, as illustrated in FIG. 8, a sling 510 can include first 590 and second 592 series of indicia that mirror each other relative to a longitudinal midpoint 580 of the sling 510. This configuration is considered advantageous at least because it facilitates centering of the sling 510 during placement. For example, if two series of color-based indicia—each comprising a set of differently-colored markers that mirrors the other—are used, a clinician can adjust the sling 510 across the tongue following initial placement in performance of a method, such as any of the methods described herein, by pulling and/or advancing each end of the sling until indicia of the same color are disposed adjacent the respective opening in the mandible, or at the same distance from the respective opening in the mandible. Once such positioning is achieved, the clinician has assurance that the sling 510 is centered or substantially centered across the tongue and is able to proceed to further secure the sling without further adjustment.

It is noted that any suitable number, configuration and arrangement of indicia can be included in a sling according to a particular embodiment and a skilled artisan will be able to construct a sling with an appropriate number, configuration and arrangement of such indicia based on various considerations, including the nature of the material from which the sling is comprised and the needs of the users expected to be placing the sling. Color-based indicia are merely exemplary, and any other suitable indicia can be used, including indicia differentiated by structure such that tactile feedback can be used to achieve a desired positioning.

Slings can include additional devices that facilitate their use. For example, FIG. 9 illustrates the sling 10 of FIGS. 1 through 3 disposed within a sheath 602. The sheath 602 is an elongate, pouched-shaped member with an open end 604 and an opposing closed end 606. The sheath 602 defines and interior chamber 608 that is sized and configured to receive one end of the sling 10. The sheath 602 advantageously fits snuggly over one end of the sling 10 such that a gentle pulling force on the sheath 602 is required to remove it from its position over the sling 10. Furthermore, the sheath 602 advantageously has an axial length that allows the sheath 602 to extend over all ribs 36 on one longitudinal portion, such as a longitudinal half, of the sling 10 when that particular portion is diposed within the interior chamber 608.

Any suitable material can be used for the sheath 602, and a skilled artisan will be able to select an appropriate material for a sling according to a particular embodiment based on various considerations, including the material of the sling and the desired handling properties of the sheath during implantation of the sling. The inventors have determined that flexible materials capable of sliding over the material of the main body of the sling provide advantageous handling characteristics. Examples of suitable flexible materials include low density polyethylene (LDPE) and other polymeric materials. The flexible material should provide a degree of flexibility that will aid in tunneling of the device during implantation, but should not roll on itself.

FIG. 10 illustrates the sling 10 of FIGS. 1 through 3 disposed within first 602 and second 610 sheaths. The first sheath 602 is the sheath illustrated in FIG. 9 and described above. The second sheath 610 is similar to the first sheath 602, and thus comprises an elongate, pouched-shaped member with an open end 612 and an opposing closed end 614. The sheath 610 defines and interior chamber 616 that is sized and configured to receive the end of the sling 610 opposite the end disposed within the first sheath 602. The sheath 610 is also advantageous sized and configured as described above for the first sheath 602, and can have the same, substantially the same, or a different size and/or configurations than that of the first sheath 602.

Inclusion of one or both sheaths 602, 610 is considered advantageous at least because the sheaths 602, 604 can be used as a leading surface for blunt dissection and tunneling during implantation of the sling 10. Using the sheaths in this manner protect the sling 10 from any contact with tissue during this process and is expected to reduce damage to the sling 10 that might otherwise occur if the sling 10 was used as a dissection and/or tunneling device during implantation.

As illustrated in FIG. 10, the inclusion of two sheaths 602, 610 that are each capable of receiving and covering about a longitudinal half of the sling 10 is considered advantageous. These two sheaths 602, 610 can easily be removed following the initial placement of the sling 10 by pulling gently on the closed ends 606, 614 with forceps, fingers, or another tool until the sheaths 602, 610 slide over the covered portion of the sling 10.

FIG. 11 is a schematic of an exemplary kit 700. The kit 700 includes a sling 710 and one or more needles 712. The sling 710 can be a sling according to any embodiment, including the sling illustrated in the Figure, which includes first and second sheaths as described above. Instructions for use 714 of the kit 700 and/or the components can also be included.

The needle(s) 712 can be any suitable needle. Advantageously, at least on of the needles 712 defines a notch adapted to engage one of the openings defined by the main body of the sling 710 included in the kit 700. Furthermore, as illustrated in FIGS. 11A and 11B, the kit 700 advantageously includes two needles 712a, 712b having notches that extend away from the respective longitudinal axis in opposite directions. The inclusion of such different needles 712a, 712b allows one to be used for a pushing technique during implantation of the sling 710 and the other to be used for a pulling technique during implantation. Inclusion of both needles 712a, 712b allows a user to select one according to personal preference. Furthermore, inclusion of both needles 712a, 712b provides a complete procedural toolkit 700 for implantations that may require use of both a pushing and a pulling technique, such as the methods of treating obstructive sleep apnea described below.

FIG. 12 is a flowchart illustration of an exemplary method 800 of treating obstructive sleep apnea (OSA). Any suitable sling according an any embodiment of the invention can be used in the method. Performance of the method results in securement of the tongue of an animal, such as a human, via the sling being looped around the tongue and secured to the mandible. With the tongue secured in this manner, it is expected that the individual being treated will experience fewer and/or reduced symptoms associated with OSA.

An initial step 802 comprises creating an opening in the mandible, such as at the mental protuberance or chin. This step can be accomplished using any suitable technique, including standard drilling techniques.

Another step 804 comprises engaging a sling with a needle such that a pushing force applied on the needle will result in the sling being advanced along with the needle, such as through a tissue. This step 802 can be accomplished using a needle having a notch directed toward the lengthwise axis of the needle and away from the distal end of the needle, such as the needle 712b illustrated in FIG. 11B. A portion of the sling, such as an edge of the main body that partially defines an opening in the main body, is disposed in the notch to facilitate the pushing of the needle and the sling as a unit.

Another step 806 comprises advancing the needle and attached sling through the opening in the mandible.

Another step 808 comprises advancing the needle and attached sling into and through a lower portion of the tongue until the distal end of the needle and an end of the sling create an opening in the back of the tongue and exit through the opening.

Another step 810 comprises advancing a second needle into the opening in the mandible. This second needle advantageously has a notch directed toward the lengthwise axis of the needle and toward the distal end of the needle, such as the needle 712a illustrated in FIG. 11A.

Another step 812 comprises advancing the second needle through a lower portion of the tongue, laterally opposite the portion through which the first needle and sling were advanced, until the distal end of the second needle creates a second opening in the back of the tongue and exits through the second opening.

Another step 814 comprises engaging the sling with the second needle, such as by disposing a portion of the sling, such as an edge of the main body that partially defines an opening in the main body, in the notch of the second needle to facilitate the pulling of the second needle and the sling through the tongue as a unit.

Another step 816 comprises pulling the second needle and the sling through the tunnel created during the step 812 of advancing the second needle through the tongue until the end of the sling that has been advanced through both portions of the tongue has exited the tunnel and ultimately exited the opening in the mandible.

Another step 818 comprises pulling the tongue toward the front of the mouth or mandible, such as by pulling on both ends of the sling, which is now looped around the back of the tongue.

Another step 820 comprises securing the sling to a tissue to support the tongue in the new position. This step can be accomplished using any suitable structures and techniques for securing materials to tissues, including installation of one or more bone screws at one or more anchor points under the mandible gum line, the use of bioadhesives, sutures, or other suitable structures and/or techniques.

An optional step 822 comprises closing the opening in the mandible, such as by sealing the opening. This step can be conducted using any suitable structure and/or technique, including the placement of bone cement in the opening.

Additional optional steps can be included as appropriate. For example, if one or more sheaths are included with the sling, a step of removing the sheath or sheaths from the sling by gently pulling the sheath or sheaths away from the sling can be included, and should be performed prior to the step of securing the sling to a tissue to support the tongue in the new position. Also, to aid in verification of a desired placement, the sling and/or the position of the tongue can be visualized prior to securement using any suitable technique, method and/or equipment, such as an appropriate endoscope.

Also, if the sling includes an elongate wire member, an optional step of removing the elongate wire member from the sling can be included, if desired. This step can be accomplished using any suitable technique, and the specific technique selected will depend on the nature of the structure of the sling. For example, if the elongate wire member contained entirely within the sling, a use can create a nick or small cut in the sling to expose a portion of the elongate wire member, and can then grasp the portion with forceps or other suitable tool and pull the portion until the elongate wire member is removed from the sling. Similarly, if a portion of the elongate wire member extends out of the sling, as described above, a user can simply grasp that portion and pull until the elongate wire member is removed from the sling.

Figure 13:
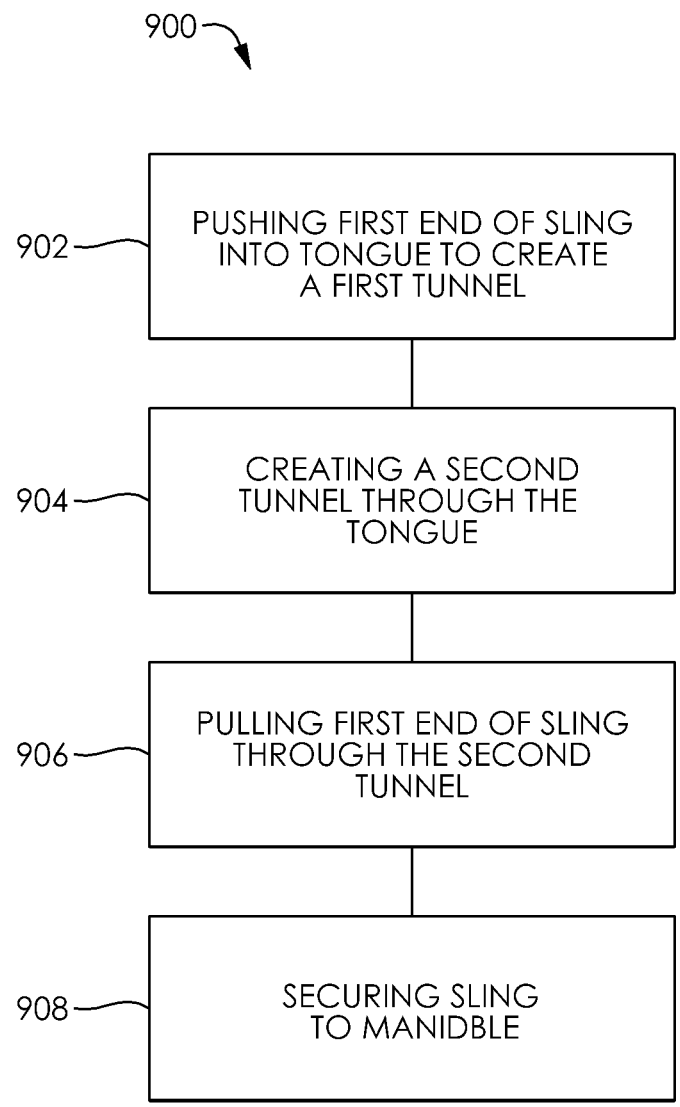
FIG. 13 is a flowchart illustration of a second exemplary method of treatment.

FIG. 13 is a flowchart illustration of another exemplary method 900 of treating obstructive sleep apnea (OSA). Any suitable sling according any embodiment of the invention can be used in the method. Performance of the method results in securement of the tongue of an animal, such as a human, via the sling being looped around the tongue and secured to the mandible. With the tongue secured in this manner, it is expected that the individual being treated will experience fewer and/or reduced symptoms associated with OSA.

An initial step 902 comprises pushing a first end of a sling into the tongue of a patient to create a first tunnel through the tongue of said patient until the first end of the sling has passed into, through and exited the tunnel at the back of the tongue relative to the chin of said patient and a second end of the sling remains outside the first tunnel.

Another step 904 comprises creating a second tunnel through the tongue of said patient. This step can be accomplished using any suitable technique, including passing a needle through the tongue of the patient. This step is advantageously performed such that the second tunnel is laterally opposite the first tunnel with respect to the lengthwise axis of the tongue, and such that the second tunnel includes an opening toward the front of the tongue and an exit at the back of the tongue, similar to the first tunnel. Also, any suitable device and/or technique can be used for this step, including a needle.

Another step 906 comprises pulling the first end of the sling through the second tunnel created in the tongue of said patient until the first end of the sling has passed through the entire length of the second tunnel and the second end of the sling remains outside the first tunnel. This step can be accomplished in any suitable manner, such as by engaging the first end of the sling with a needle used to form the second tunnel in step 904.

Another step 908 comprises securing the sling to the mandible of said patient such that the tongue of said patient is pulled toward the chin of said patient by the sling. This step can be accomplished in any suitable manner, including by securing the first and second ends of the sling to the mandible at one or more anchor points along the mandible gum line.

Figure 14:
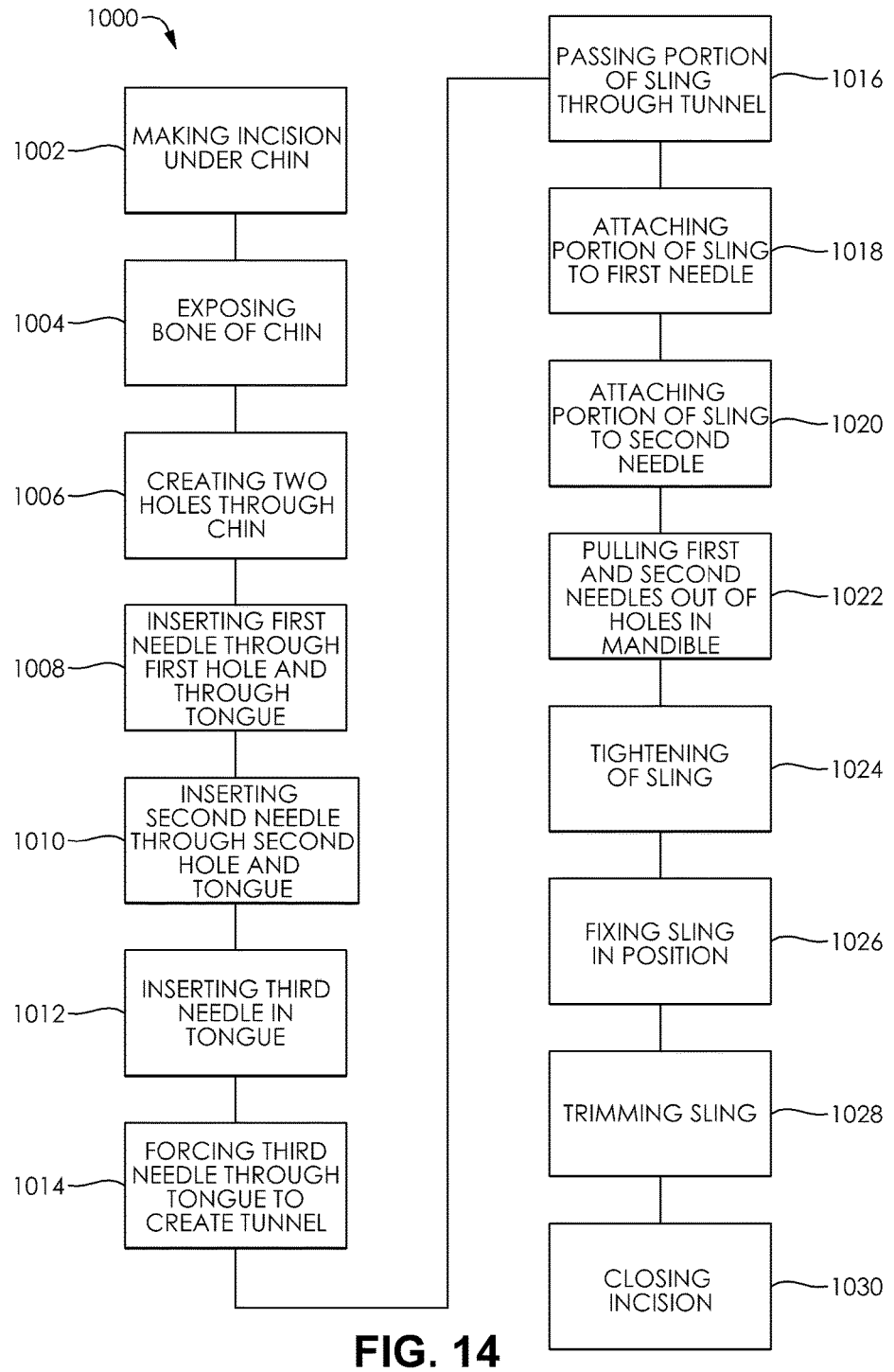
FIG. 14 is a flowchart illustration of a third exemplary method of treatment.

FIG. 14 is a flowchart illustration of another exemplary method 1000 of treating obstructive sleep apnea (OSA). Any suitable sling according any embodiment of the invention can be used in the method. Performance of the method results in securement of the tongue of an animal, such as a human, via the sling being looped through the tongue and secured to the mandible. With the tongue secured in this manner, it is expected that the individual being treated will experience fewer and/or reduced symptoms associated with OSA.

This exemplary method 1000 is considered particularly advantageous at least because it causes minimal aesthetic scaring for the patient, and any resulting scar is positioned under the chin and not on the front of the face. Furthermore, this method causes relatively minor perforations at the back of the tongue to facilitate the exchange on the sling between the needles used in the procedure.

Figure 15:
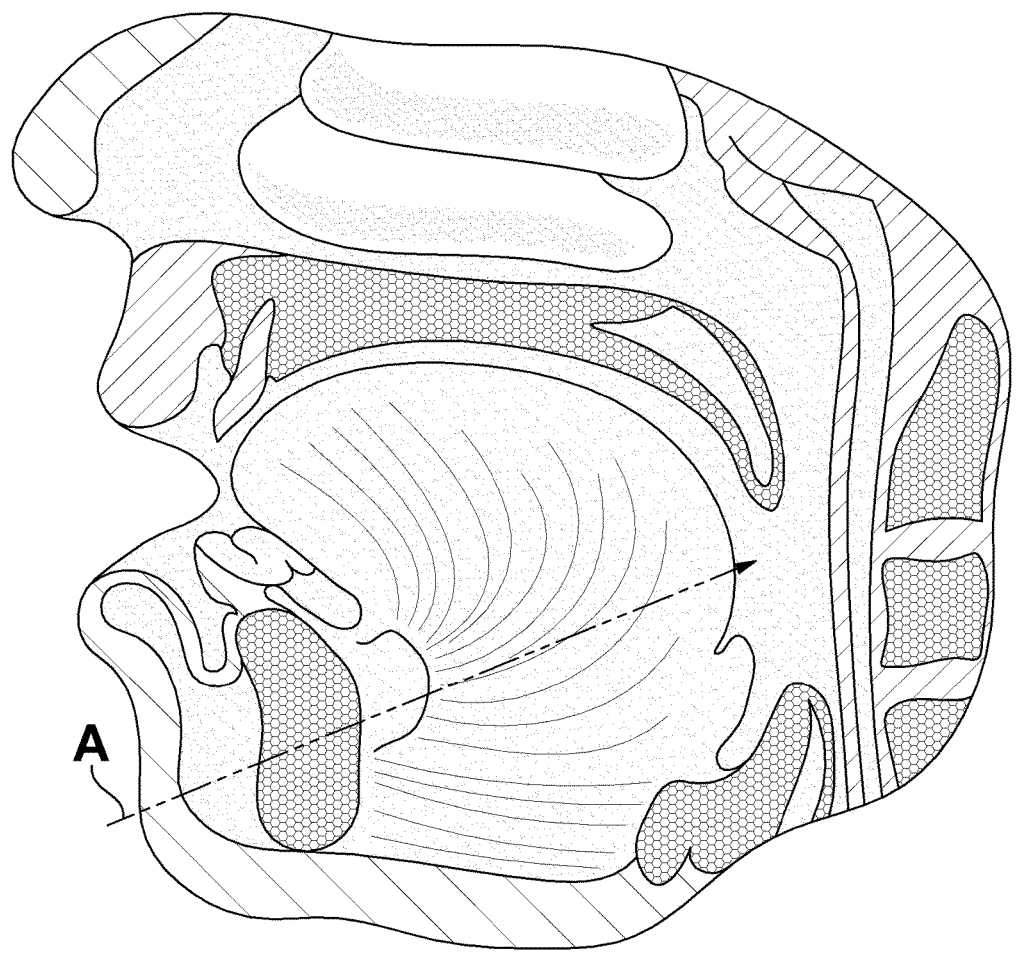
FIG. 15 is a schematic illustration showing a location for an incision made during performance of the method illustrated in FIG. 1.

An initial step 1002 comprises making an incision under the chin of a patient. The incision can be made at any suitable location that allows for the drilling of holes, as described below. FIG. 15 is a schematic illustration of a suitable location for the incision. Any suitable tool can be used to make the incision.

Another step 1004 comprises moving the skin located adjacent the incision made in step 1002 to expose the bone of the chin. Any suitable tool can be used to move the skin.

Another step 1006 comprises creating two separate holes through the chin of the mandible, such as by drilling through the mandible. The holes can be drilled using a suitable bone drilling tool, and each hole should be of a sufficient diameter to allow passage or a portion of the sling through the hole, as described below. Also, it is considered advantageous to drill the holes as close together as possible while retaining distinctness to facilitate tightening of the sling, as described below. Furthermore, to facilitate positioning of the sling relative to the tongue, the holes should be drilled with a slight upward angle. The holes can be made through the mental protuberance of the chin. Arrow A in FIG. 15 represents a suitable location and axis for the holes.

A block with pre-drilled holes positioned at a desired angle and/or distance from each other can be used to guide the drilling of the holes through the mandible. Use of such a block, while considered optional, is considered advantageous at least because it is expected to reduce risk of error in the positioning of the holes.

As an alternative, a single hole with two sub-channels that exit the back of the mandible near the tongue could also be formed. Furthermore, a single hole could be formed. The use of two separate and distinct holes is considered advantageous, though, at least because of the relative ease of formation and provision of separate passageways for the separate ends of the sling, as described more fully below.

Another step 1008 comprises inserting a pull needle through the first of the holes drilled in step 1006 and passing the needle through the tongue until the tip of the needle forms a perforation at the back of the tongue. The performance of this step will create a tunnel through the tongue. It is considered advantageous to conduct this step such that the tunnel is formed in a medial to lateral manner on the side of the tongue that corresponds to the hole through which the pull needle has been inserted.

Another step 1010 comprises inserting a second pull needle through the second of the holes drilled in step 1006 and passing the needle through the tongue until the tip of the needle forms a second perforation at the back of the tongue. The performance of this step will create a second tunnel through the tongue. Similar to step 1008, it is considered advantageous to conduct this step such that the second tunnel is formed in a medial to lateral manner on the side of the tongue that corresponds to the second hole through which the second pull needle has been inserted.

Another step 1012 comprises inserting a push needle having a first end of a sling attached to it into the first perforation formed in the back of the tongue in step 1008. The tip of the first pull needle can be used to guide the push needle and attached sling into the first perforation.

Once inserted into the first perforation, another step 1014 comprises forcing the tip of the push needle through the base of the tongue along an axis and to the second perforation formed in step 1010. The performance of this step creates a third tunnel through the tongue that extends from the first perforation to the second perforation.

Once the tip of the push needle reaches the second perforation, another step 1016 comprises passing a portion of the sling through the third tunnel. This step is advantageously performed until the sling is disposed through the third tunnel with approximately half of its length positioned on each side of the tongue.

Once a desired positioning of the sling is achieved, another step 1018 comprises attaching a portion of the sling to the first pull needle at the back of the tongue. Any suitable attachment member and/or technique can be used to accomplish this step, and a skilled artisan will be able to select an appropriate attachment member and/or technique for a particular method based on various considerations, including the nature of the sling being used. A direct attachment between the sling and the pull needle can be used (e.g., securing a notch of the pull needle to a portion of the sling, such as an edge adjacent an opening). Also, a suture with a knot can be looped around a portion of the sling and secured in a notch of the pull needle.

Another step 1020 comprises attaching a portion of the sling to the second pull needle at the back of the tongue. This step is similar to step 1018 and can be conducted in the same or different manner (e.g., using the same or different attachment member and/or technique).

After both steps 1018 and 1020 have been conducted, another step 1022 comprises pulling the pull needles through the respective tunnels in the tongue and out of the respective hole in the mandible. It is considered advantageous to perform this step by pulling each of the needles simultaneously and at substantially the same rate with substantially the same force, but the needles can be pulled sequentially or with different rates and/or forces if considered desirable and/or necessary. Performance of this step results in each of the ends of the sling being pulled through one of the first and second tunnels in the tongue. At the end of performance of this step, the ends of the slings extend outward from the holes in the mandible and the central portion of the sling is looped around the base of the tongue.

After completion of step 1022, a step 1024 of tightening the sling by pulling on the ends of the sling can be performed. This can be performed until a desired placement of the tongue relative to the front of the mouth and/or the mandible is achieved.

Another step 1026 comprises fixing the sling in position within each of the holes. This step can be accomplished using any suitable material, attachment member, and/or technique. An application of bone cement into each of the holes is considered suitable.

Another step 1028 of trimming the sling, such as by cutting the portion or portions of the sling that extend outward from the holes, can be performed. If included, it is considered advantageous to include this step after completion of step 1026. Furthermore, it is considered advantageous to perform this step after a desired positioning and/or tensioning is achieved, such as after completion of step 1024.

Another step 1030 of closing the incision under the chin can be included. This step can be performed using any suitable attachment member and or technique, such as sutures and clips.

Figure 16:
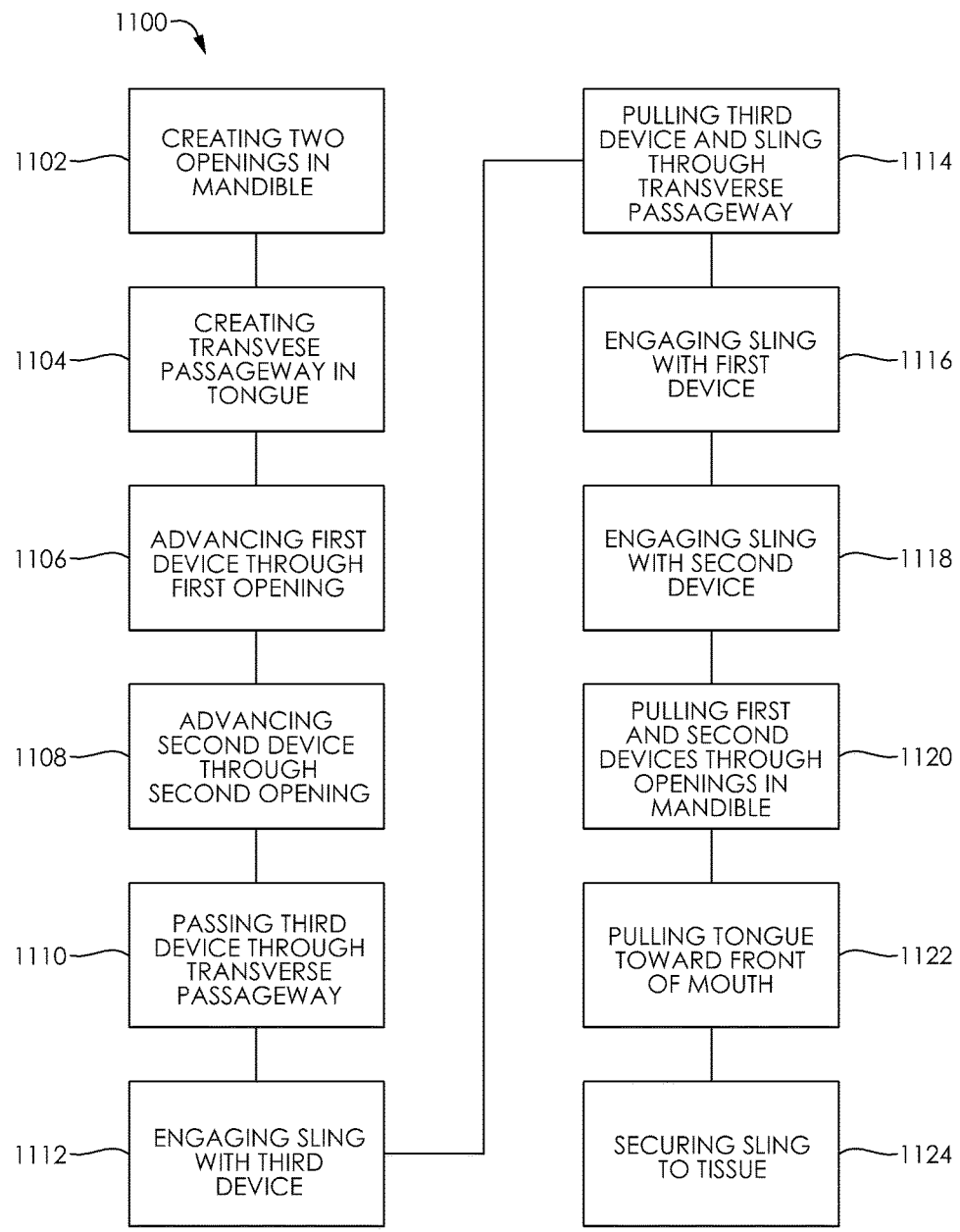
FIG. 16 is a flowchart illustration of a fourth exemplary method of treatment.

FIG. 16 is a flowchart illustration of another exemplary method 1100 of treating obstructive sleep apnea (OSA). Any suitable sling according to any embodiment of the invention can be used in the method. Performance of the method results in securement of the tongue of an animal, such as a human, via the sling being looped through the tongue and secured to the mandible. With the tongue secured in this manner, it is expected that the individual being treated will experience fewer and/or reduced symptoms associated with OSA.

An initial step 1102 comprises creating two openings in the mandible of the patient, such as at the mental protuberance or chin. This step can be accomplished using any suitable technique, including standard drilling techniques. It is considered advantageous to drill the holes as close together as possible while retaining distinctness to facilitate tightening of the sling, as described below. Furthermore, to facilitate positioning of the sling relative to the tongue, the holes should be drilled with a slight upward angle and directed toward the back or base of the tongue. The arrow in FIG. 15 represents a suitable location and axis for the holes.

Another step 1104 comprises creating a passageway in the tongue of a patient such that the passageway lies on a plane that is transverse to the longitudinal axis of the tongue. Any suitable technique and tool can be used to perform this step, including a needle or other tunneling instrument.

Another step 1106 comprises advancing a first device through the first of the two openings in the mandible such that the device extends through the entire opening, with a portion of the device outside of the opening and adjacent the chin and another portion of the device outside of the opening and adjacent the tongue. Any suitable device can be used and need only be able to fit in and movable through the opening. A device with structural adaptations, such as a hook or other suitable structure, can be used to facilitate engagement of the sling, as described below.

Another step 1108 comprises advancing a second device through the second of the two openings in the mandible such that the second device extends through the entire second opening, with a portion of the second device outside of the second opening and adjacent the chin and another portion of the second device outside of the second opening and adjacent the tongue. Any suitable device can be used and need only be able to fit in and movable through the second opening. A device with structural adaptations, such as a hook or other suitable structure, can be used to facilitate engagement of the sling, as described below.

Another step 1110 comprises passing a device through the passageway in the tongue such that a portion of the device extends beyond one end of the passageway and another portion of the device extends beyond another end of the passageway. Any suitable device can be used and need only be able to fit in and movable through the second opening. A device with structural adaptations, such as a hook or other suitable structure, can be used to facilitate engagement of the sling, as described below.

Another step 1112 comprises engaging a sling according to an embodiment with one end of the device disposed through the passageway in the tongue.

Another step 1114 comprises pulling the device disposed through the passageway in the tongue and the attached sling through the passageway in the tongue until the sling is disposed in the passageway with a portion of the sling extending beyond one end of the passageway and another portion of the sling extending beyond another end of the passageway.

Another step 1116 comprises engaging a first portion of the sling, such as the first end of the sling, with the tongue-adjacent end of the first device disposed in the first of the two openings in the mandible such that a pulling force applied to the first device will result in the first end of the sling being pulled along with the first device through the first opening in the mandible.

Another step 1118 comprises engaging a second portion of the sling, such as the second end of the sling, with the tongue-adjacent end of the second device disposed in the second of the two openings in the mandible such that a pulling force applied to the second device will result in the second end of the sling being pulled along with the second device through the second opening in the mandible.

Another step 1120 comprises pulling the first and second devices and the first and second ends of the sling through the respective openings in the mandible until each end of the sling has exited the respective opening.

Another step 1122 comprises pulling the tongue toward the front of the mouth or mandible by pulling on one or both of the first and second devices and/or one or both of the first and second ends of the sling.

Another step 1124 comprises securing the sling to a tissue, such as the mandible, to support the tongue in the new position. Optionally, another step can comprise sealing the openings in the mandible, such as with bone cement or other suitable composition and/or technique.

Figure 17:
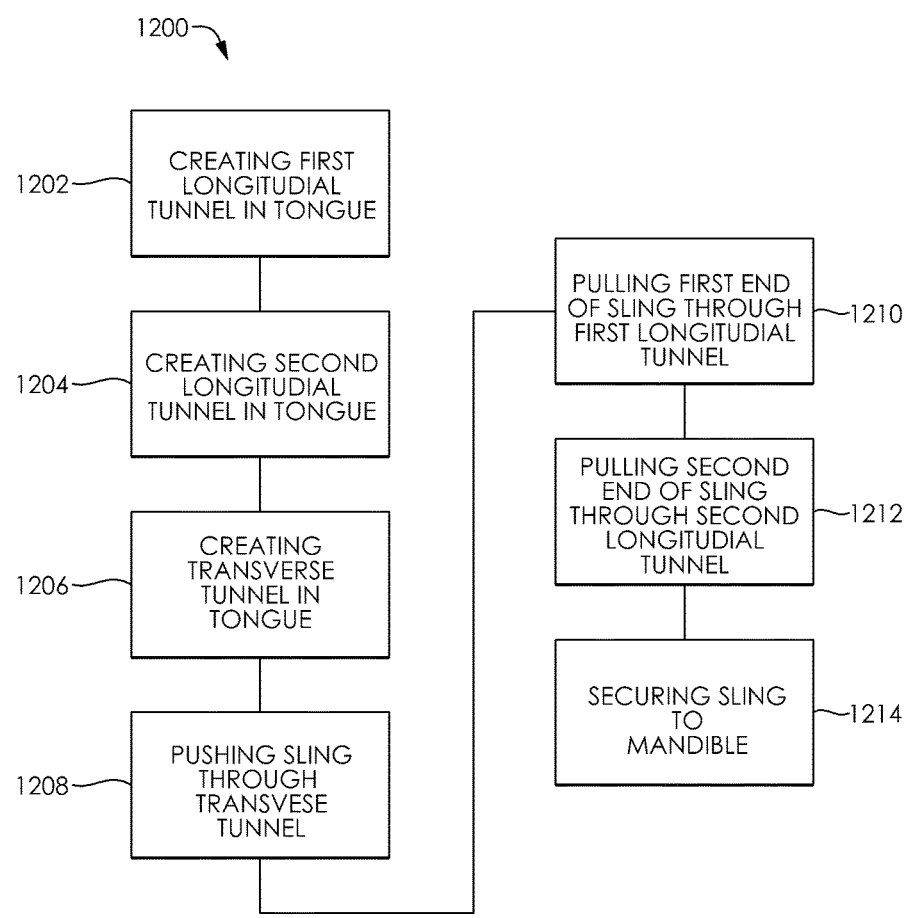
FIG. 17 is a flowchart illustration of a fifth exemplary method of treatment.

FIG. 17 is a flowchart illustration of another exemplary method 1200 of treating obstructive sleep apnea (OSA). Any suitable sling according any embodiment of the invention can be used in the method. Performance of the method results in securement of the tongue of an animal, such as a human, via the sling being looped through the tongue and secured to the mandible. With the tongue secured in this manner, it is expected that the individual being treated will experience fewer and/or reduced symptoms associated with OSA.

An initial step 1202 comprises creating a first longitudinal tunnel in the tongue. This step can be accomplished using any suitable technique and device, such as a needle. The step is advantageously performed such that a tunnel is formed through the tongue that extends upward from a position on the lower surface of the anterior portion of the tongue to a position on the opposite surface on the posterior or base portion of the tongue. Arrow A in FIG. 15 represents a suitable location and axis for the first longitudinal tunnel.

Another step 1204 comprises creating a second longitudinal tunnel in the tongue. This step can be accomplished using any suitable technique and device, such as a needle. The step is advantageously performed such that a second tunnel is formed through the tongue that extends upward from a second position on the lower surface of the anterior portion of the tongue to a second position on the opposite surface on the posterior or base portion of the tongue. Arrow A in FIG. 15 represents a suitable location and axis for the first longitudinal tunnel. The axis of the second tunnel advantageously lies on the same or substantially the same plane as the axis of the first tunnel, but it is not necessary that the tunnels have this structural arrangement.

Another step 1206 comprises creating a transverse tunnel in the tongue. This step can be accomplished using any suitable technique and device, such as a needle. The step is advantageously performed such that the axis of the transverse tunnel is substantially orthogonal to an axis of one or both of the first and second longitudinal tunnels, although this structural arrangement of the tunnels is not necessary. Indeed, the transverse tunnel can be formed such that its axis extends at any angle to the longitudinal axis of the tongue. Advantageously, the transverse tunnel extends across the posterior surface of the tongue, opposite the mandible, in the mid-region or base of the tongue.

Another step 1208 comprises advancing a sling through the transverse tunnel such that a portion of the sling is disposed in the transverse tunnel and such that the first end of the sling extends outward from an end of the transverse tunnel and the second end of the sling extends outward from the other end of the transverse tunnel. This step can be accomplished using any suitable sling, such as any of the embodiments described and illustrated herein, and any suitable technique and device, such as a needle. This step can be accomplished by pushing the sling through the transverse tunnel or by pulling the sling through the transverse tunnel, and a skilled artisan will be able to select a suitable approach in the performance of a particular method based on various considerations, including the nature of the sling being used and the space available in the cavity within which the sling is being placed.

Another step 1210 comprises pulling the first end of the sling through the first longitudinal tunnel. This step can be accomplished using any suitable technique and device, such as a needle, clamp or other device adapted to engage a portion of the sling and hold the portion while pulling the portion through a tunnel.

Another step comprises pulling the second end of the sling through the second longitudinal tunnel. This step can be accomplished using any suitable technique and device, such as a needle, clamp or other device adapted to engage a portion of the sling and hold the portion while pulling the portion through a tunnel.

Another step 1214 comprises securing the sling to a tissue, such as the mandible or tissue located in the mouth, to support the tongue in the new position. This step advantageously comprises securing a first portion of the sling to the tissue and securing a second portion of the sling to the same or different tissue. Any suitable technique, devices, and/or apparatuses can be used to accomplish the securing, including bone cement, adhesives, and sutures and other mechanical attachment members.

The foregoing detailed description refers to exemplary occlusion devices and includes the best mode for practicing the invention. The description and the appended drawings illustrating the described devices are intended only to provide examples and not to limit the scope of the claims in any manner.

What is claimed is:

1. A sling, comprising:
    a main body extending along a lengthwise axis and having first and second opposing ends, a longitudinal midpoint, first and second opposing sides, first and second opposing surfaces, and a first portion extending along the lengthwise axis, the first portion having a first portion first end, a first portion second end, and a first width extending from the first side to the second side orthogonally to the lengthwise axis and through the longitudinal midpoint, the first width extending from the first portion first end to the first portion second end and along the lengthwise axis a first length;
    the first end defining a first end loop defining a first passageway extending through the main body from the first surface to the second surface, the first end having a second width extending orthogonally to the lengthwise axis, the second width disposed on a second portion extending from the first portion first end to the first end, the second portion having a second length along the lengthwise axis that is less than the first length; and
    the second end defining a second end loop defining a second passageway extending through the main body from the first surface to the second surface, the second end having a third width extending orthogonally to the lengthwise axis, the third width disposed on a third portion extending from the first portion second end to the second end, the third portion having a third length along the lengthwise axis that is less than the first length;
    wherein one of the second and third widths is greater than the first width; and
    wherein the main body defines an opening extending through the first portion of the main body that has the first width and from the first surface to the second surface;
    further comprising a radiopaque marker disposed on the lengthwise axis at the longitudinal midpoint.

2. The sling of claim 1, wherein the main body comprises a polymeric material.

3. The sling of claim 1, wherein the main body comprises a remodelable material.

4. The sling of claim 3, wherein the remodelable material comprises an extracellular matrix material.

5. The sling of claim 4, wherein the extracellular matrix material comprises small intestine submucosa (SIS).

6. The sling of claim 1, wherein the main body comprises a multilaminate construct.

7. The sling of claim 6, wherein the main body is formed of multiple layers of remodelable material.

8. The sling of claim 7, wherein the remodelable material comprises an extracellular matrix material.

9. The sling of claim 8, wherein the extracellular matrix material comprises small intestine submucosa.

10. The sling of claim 1, wherein the first passageway has a fourth width extending orthogonally to the lengthwise axis; and
    wherein the opening has a fifth width extending orthogonally to the lengthwise axis; and
    wherein the fourth width is greater than the fifth width.

11. The sling of claim 10, wherein the second passageway has a sixth width extending orthogonally to the lengthwise axis; and
    wherein the sixth width is greater than the fifth width.

12. The sling of claim 1, wherein each of the second and third widths is greater than the first width.

* * * * *